United States Patent
McDermott et al.

(10) Patent No.: US 11,786,652 B2
(45) Date of Patent: Oct. 17, 2023

(54) SYSTEM AND METHOD FOR DRIVE MEMBER POSITION AND FLUID INJECTOR SYSTEM MECHANICAL CALIBRATION

(71) Applicant: BAYER HEALTHCARE LLC, Whippany, NJ (US)

(72) Inventors: Michael McDermott, Pittsburgh, PA (US); Chelsea Marsh, Pittsburgh, PA (US); Michael Spohn, Fenelton, PA (US); William Barone, Pittsburgh, PA (US); Shahab Taheri, The Ponds (AU); Han Min Thu, Mandalay (MM); David Coleman, North Parramatta (AU); Jee Hoon Yoo, St. Ermington (AU); Vince Delbrugge, Indiana, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 718 days.

(21) Appl. No.: 16/623,828

(22) PCT Filed: Aug. 28, 2018

(86) PCT No.: PCT/US2018/048284
§ 371 (c)(1),
(2) Date: Dec. 18, 2019

(87) PCT Pub. No.: WO2019/046261
PCT Pub. Date: Mar. 7, 2019

(65) Prior Publication Data
US 2020/0179595 A1 Jun. 11, 2020

Related U.S. Application Data

(60) Provisional application No. 62/552,589, filed on Aug. 31, 2017, provisional application No. 62/552,427, filed on Aug. 31, 2017.

(51) Int. Cl.
*A61M 5/145* (2006.01)
*A61M 5/14* (2006.01)
(Continued)

(52) U.S. Cl.
CPC .... *A61M 5/14546* (2013.01); *A61M 5/14566* (2013.01); *A61M 5/1408* (2013.01);
(Continued)

(58) Field of Classification Search
CPC .......... A61M 5/14546; A61M 5/14566; A61M 5/16827; A61M 5/16881;
(Continued)

(56) References Cited

U.S. PATENT DOCUMENTS

| 383,858 | A | 6/1888 | Campbell |
| 508,584 | A | 11/1893 | Stevens |

(Continued)

FOREIGN PATENT DOCUMENTS

| CA | 2045070 A1 | 2/1992 |
| CA | 2077712 A1 | 12/1993 |

(Continued)

OTHER PUBLICATIONS

Angelini, P., "Use of mechanical injectors during percutaneous transluminal coronary angioplasty (PTCA)," Catheterization and Cardiovascular Diagnosis, vol. 16, Issue 3, pp. 193-194, Mar. 1989.
(Continued)

*Primary Examiner* — James D Ponton
*Assistant Examiner* — Neeraja Gollamudi
(74) *Attorney, Agent, or Firm* — David Schramm; Joseph L. Kent; James R. Stevenson

(57) ABSTRACT

The present disclosure provides improved methods for calibrating the zero position of at least one drive member of an injector system is disclosed. Automated methods of position calibration of the drive member of a fluid injector are
(Continued)

disclosed. These methods address sources of error in positional accuracy and fluid delivery inaccuracies, such as disposable syringe tolerance and injector wear over time. According to other embodiments of the present disclosure, methods and fluid injector systems for determining and correcting for the amount of slack in a fluid injection apparatus are described. An understanding of the calibration and the amount of slack in a fluid injection system allows a processor to correct for the slack, thereby ensuring more accurate fluid delivery to the patient and more accurate imaging processes.

8 Claims, 16 Drawing Sheets

(51) Int. Cl.
 A61M 5/168 (2006.01)
 A61M 5/142 (2006.01)
(52) U.S. Cl.
 CPC ..... A61M 5/16827 (2013.01); A61M 5/16881 (2013.01); A61M 2005/14208 (2013.01); A61M 2005/14553 (2013.01); A61M 2205/332 (2013.01); A61M 2205/3306 (2013.01); A61M 2205/3561 (2013.01)
(58) Field of Classification Search
 CPC ......... A61M 2005/14208; A61M 2005/14553; A61M 2205/3306; A61M 2205/332; A61M 2205/3561; A61M 5/31556; A61M 5/31573
 See application file for complete search history.

(56) References Cited

U.S. PATENT DOCUMENTS

| | | |
|---|---|---|
| 945,143 A | 1/1910 | Iacques |
| 2,511,291 A | 6/1950 | Mueller |
| 2,583,206 A | 1/1952 | Borck et al. |
| 3,156,236 A | 11/1964 | Williamson |
| 3,159,312 A | 12/1964 | Van Sciver, II |
| 3,276,472 A | 10/1966 | Jinkens et al. |
| 3,349,713 A | 10/1967 | Fassbender |
| 3,520,295 A | 7/1970 | Paul |
| 3,523,523 A | 8/1970 | Heinrich et al. |
| 3,623,474 A | 11/1971 | Heilman et al. |
| 3,635,444 A | 1/1972 | Potter |
| 3,671,208 A | 6/1972 | Wayne |
| 3,701,345 A | 10/1972 | Heilman |
| 3,719,207 A | 3/1973 | Takeda |
| 3,755,655 A | 8/1973 | Senegal |
| 3,793,600 A | 2/1974 | Grosbard |
| 3,812,843 A | 5/1974 | Wootten et al. |
| 3,817,843 A | 6/1974 | Barrett |
| 3,839,708 A | 10/1974 | Lyons et al. |
| 3,868,967 A | 3/1975 | Harding |
| 3,888,239 A | 6/1975 | Rubinstein |
| 3,895,220 A | 7/1975 | Nelson et al. |
| 3,898,983 A | 8/1975 | Elam |
| 3,927,955 A | 12/1975 | Spinosa et al. |
| 3,941,126 A | 3/1976 | Dietrich et al. |
| 3,958,103 A | 5/1976 | Oka et al. |
| 3,968,195 A | 7/1976 | Bishop |
| 3,995,381 A | 12/1976 | Manfred et al. |
| 4,001,549 A | 1/1977 | Corwin |
| 4,006,736 A | 2/1977 | Kranys et al. |
| 4,038,981 A | 8/1977 | Lefevre et al. |
| 4,044,757 A | 8/1977 | McWhorter et al. |
| 4,090,502 A | 5/1978 | Tajika |
| 4,135,247 A | 1/1979 | Gordon et al. |
| 4,151,845 A | 5/1979 | Clemens |
| 4,187,057 A | 2/1980 | Xanthopoulos |
| 4,191,183 A | 3/1980 | Mendelson |
| 4,199,000 A | 4/1980 | Edstrom |
| 4,204,775 A | 5/1980 | Speer |
| 4,207,871 A | 6/1980 | Jenkins |
| 4,208,136 A | 6/1980 | King et al. |
| 4,223,675 A | 9/1980 | Williams |
| 4,262,824 A | 4/1981 | Hrynewycz |
| 4,263,916 A | 4/1981 | Brooks et al. |
| 4,280,494 A | 7/1981 | Cosgrove, Jr. et al. |
| 4,284,073 A | 8/1981 | Krause et al. |
| 4,315,247 A | 2/1982 | Germanton |
| 4,319,568 A | 3/1982 | Tregoning |
| 4,329,067 A | 5/1982 | Goudy, Jr. |
| 4,340,153 A | 7/1982 | Spivey |
| 4,341,153 A | 7/1982 | Bowser |
| 4,392,847 A | 7/1983 | Whitney et al. |
| 4,392,849 A | 7/1983 | Petre et al. |
| 4,396,385 A | 8/1983 | Kelly et al. |
| 4,402,310 A | 9/1983 | Kimura |
| 4,409,966 A | 10/1983 | Lambrecht et al. |
| 4,434,820 A | 3/1984 | Glass |
| 4,434,822 A | 3/1984 | Bellamy et al. |
| 4,441,823 A | 4/1984 | Power et al. |
| 4,444,198 A | 4/1984 | Petre |
| 4,447,230 A | 5/1984 | Gula et al. |
| 4,448,200 A | 5/1984 | Brooks et al. |
| 4,474,476 A | 10/1984 | Thomsen |
| 4,477,923 A | 10/1984 | Baumann et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,504,908 A | 3/1985 | Riederer et al. |
| 4,509,526 A | 4/1985 | Barnes et al. |
| 4,512,764 A | 4/1985 | Wunsch |
| 4,542,459 A | 9/1985 | Riederer |
| 4,544,949 A | 10/1985 | Kurihara |
| 4,551,133 A | 11/1985 | Zegers et al. |
| 4,552,130 A | 11/1985 | Kinoshita |
| 4,559,036 A | 12/1985 | Wunsch |
| 4,563,175 A | 1/1986 | LaFond |
| 4,578,802 A | 3/1986 | Itoh |
| 4,585,009 A | 4/1986 | Barker et al. |
| 4,585,941 A | 4/1986 | Bergner |
| 4,610,670 A | 9/1986 | Spencer |
| 4,610,790 A | 9/1986 | Reti et al. |
| 4,611,340 A | 9/1986 | Okazaki |
| 4,612,572 A | 9/1986 | Komatsu et al. |
| 4,625,494 A | 12/1986 | Iwatschenko et al. |
| 4,626,144 A | 12/1986 | Berner |
| 4,633,307 A | 12/1986 | Honda |
| 4,634,426 A | 1/1987 | Kamen |
| 4,636,144 A | 1/1987 | Abe et al. |
| 4,655,197 A | 4/1987 | Atkinson |
| 4,662,906 A | 5/1987 | Matkovich et al. |
| 4,672,651 A | 6/1987 | Horiba et al. |
| 4,676,776 A | 6/1987 | Howson |
| 4,682,170 A | 7/1987 | Kubota et al. |
| 4,689,670 A | 8/1987 | Okazaki |
| 4,710,166 A | 12/1987 | Thompson et al. |
| 4,723,261 A | 2/1988 | Janssen et al. |
| 4,750,643 A | 6/1988 | Wortrich |
| 4,754,786 A | 7/1988 | Roberts |
| 4,781,687 A | 11/1988 | Wall |
| 4,783,273 A | 11/1988 | Knutsson et al. |
| 4,789,014 A | 12/1988 | Digianfilippo et al. |
| 4,793,357 A | 12/1988 | Lindstrom |
| 4,795,429 A | 1/1989 | Feldstein |
| 4,798,590 A | 1/1989 | O'Leary et al. |
| 4,804,454 A | 2/1989 | Asakura et al. |
| 4,823,833 A | 4/1989 | Hogan et al. |
| 4,835,521 A | 5/1989 | Andrejasich et al. |
| 4,836,187 A | 6/1989 | Iwakoshi et al. |
| 4,838,856 A | 6/1989 | Mulreany et al. |
| 4,840,620 A | 6/1989 | Kobayashi et al. |
| 4,844,052 A | 7/1989 | Iwakoshi et al. |
| 4,853,521 A | 8/1989 | Claeys et al. |
| 4,854,301 A | 8/1989 | Nakajima |
| 4,854,324 A | 8/1989 | Hirschman et al. |
| 4,857,056 A | 8/1989 | Talonn |

(56) References Cited

U.S. PATENT DOCUMENTS

| | | |
|---|---|---|
| 4,874,359 A | 10/1989 | White et al. |
| 4,879,880 A | 11/1989 | Harrison |
| 4,880,014 A | 11/1989 | Zarowitz et al. |
| 4,887,208 A | 12/1989 | Schneider et al. |
| 4,887,554 A | 12/1989 | Whitford |
| 4,901,731 A | 2/1990 | Millar |
| 4,903,705 A | 2/1990 | Imamura et al. |
| 4,913,154 A | 4/1990 | Ermert et al. |
| 4,922,916 A | 5/1990 | Ermert et al. |
| 4,925,444 A | 5/1990 | Orkin et al. |
| 4,929,818 A | 5/1990 | Bradbury et al. |
| 4,935,005 A | 6/1990 | Haines |
| 4,936,832 A | 6/1990 | Vaillancourt |
| 4,943,279 A | 7/1990 | Samiotes et al. |
| 4,943,779 A | 7/1990 | Pedersen et al. |
| 4,943,987 A | 7/1990 | Asahina et al. |
| 4,946,256 A | 8/1990 | Woodruff |
| 4,946,439 A | 8/1990 | Eggers |
| 4,947,412 A | 8/1990 | Mattson |
| 4,950,245 A | 8/1990 | Brown et al. |
| 4,952,068 A | 8/1990 | Flint |
| 4,954,129 A | 9/1990 | Giuliani et al. |
| 4,965,726 A | 10/1990 | Heuscher et al. |
| 4,966,579 A | 10/1990 | Polaschegg |
| 4,976,687 A | 12/1990 | Martin |
| 4,978,335 A | 12/1990 | Arthur |
| 4,981,467 A | 1/1991 | Bobo, Jr. et al. |
| 4,995,064 A | 2/1991 | Wilson et al. |
| 5,002,055 A | 3/1991 | Merki et al. |
| 5,004,472 A | 4/1991 | Wallace et al. |
| 5,009,654 A | 4/1991 | Minshall et al. |
| 5,010,473 A | 4/1991 | Jacobs |
| 5,013,173 A | 5/1991 | Shiraishi |
| 5,018,173 A | 5/1991 | Komai et al. |
| 5,032,112 A | 7/1991 | Fairchild et al. |
| 5,034,987 A | 7/1991 | Fujimoto et al. |
| 5,040,537 A | 8/1991 | Katakura |
| 5,053,002 A | 10/1991 | Barlow |
| 5,054,044 A | 10/1991 | Audon et al. |
| 5,056,568 A | 10/1991 | Digianfilippo et al. |
| 5,059,171 A | 10/1991 | Bridge et al. |
| 5,059,173 A | 10/1991 | Sacco |
| 5,061,243 A | 10/1991 | Winchell et al. |
| 5,069,662 A | 12/1991 | Bodden |
| 5,078,683 A | 1/1992 | Sancoff et al. |
| 5,088,981 A | 2/1992 | Howson et al. |
| 5,100,380 A | 3/1992 | Epstein et al. |
| 5,104,374 A | 4/1992 | Bishko et al. |
| 5,104,387 A | 4/1992 | Pokorney et al. |
| 5,108,365 A | 4/1992 | Woods, Jr. |
| 5,111,492 A | 5/1992 | Klausz |
| 5,113,905 A | 5/1992 | Pruitt et al. |
| 5,123,056 A | 6/1992 | Wilson |
| 5,123,121 A | 6/1992 | Broersma |
| 5,125,018 A | 6/1992 | Asahina |
| 5,128,121 A | 7/1992 | Berg et al. |
| 5,133,336 A | 7/1992 | Savitt et al. |
| 5,135,000 A | 8/1992 | Akselrod et al. |
| 5,140,862 A | 8/1992 | Pappalardo |
| 5,150,292 A | 9/1992 | Hoffmann et al. |
| 5,166,961 A | 11/1992 | Brunnett et al. |
| 5,180,895 A | 1/1993 | Briggs et al. |
| 5,180,896 A | 1/1993 | Gibby et al. |
| 5,190,744 A | 3/1993 | Rocklage et al. |
| 5,191,878 A | 3/1993 | Iida et al. |
| 5,196,007 A | 3/1993 | Ellman et al. |
| 5,199,604 A | 4/1993 | Palmer et al. |
| 5,207,642 A | 5/1993 | Orkin et al. |
| 5,215,095 A | 6/1993 | Macvicar et al. |
| 5,228,070 A | 7/1993 | Mattson |
| 5,230,614 A | 7/1993 | Zanger et al. |
| 5,242,390 A | 9/1993 | Goldrath |
| 5,249,122 A | 9/1993 | Stritzke |
| 5,249,579 A | 10/1993 | Hobbs et al. |
| 5,262,946 A | 11/1993 | Heuscher |
| 5,267,174 A | 11/1993 | Kaufman et al. |
| 5,269,756 A | 12/1993 | Dryden |
| 5,273,537 A | 12/1993 | Haskvitz et al. |
| 5,274,218 A | 12/1993 | Urata et al. |
| 5,276,614 A | 1/1994 | Heuscher |
| 5,286,252 A | 2/1994 | Tuttle et al. |
| 5,287,273 A | 2/1994 | Kupfer et al. |
| 5,295,967 A | 3/1994 | Rondelet et al. |
| 5,300,031 A | 4/1994 | Neer et al. |
| 5,301,656 A | 4/1994 | Negoro et al. |
| 5,301,672 A | 4/1994 | Kalender |
| 5,304,126 A | 4/1994 | Epstein et al. |
| 5,310,997 A | 5/1994 | Roach et al. |
| 5,311,568 A | 5/1994 | McKee, Jr. et al. |
| 5,313,992 A | 5/1994 | Grabenkort |
| 5,317,506 A | 5/1994 | Coutre et al. |
| 5,328,463 A | 7/1994 | Barton et al. |
| 5,329,459 A | 7/1994 | Kaufman et al. |
| 5,334,141 A | 8/1994 | Carr et al. |
| 5,339,799 A | 8/1994 | Kami et al. |
| 5,349,625 A | 9/1994 | Born et al. |
| 5,349,635 A | 9/1994 | Scott |
| 5,352,979 A | 10/1994 | Conturo |
| 5,354,273 A | 10/1994 | Hagen |
| 5,361,761 A | 11/1994 | Van et al. |
| 5,362,948 A | 11/1994 | Morimoto |
| 5,368,562 A | 11/1994 | Blomquist et al. |
| 5,368,567 A | 11/1994 | Lee |
| 5,368,570 A | 11/1994 | Thompson et al. |
| 5,373,231 A | 12/1994 | Boll et al. |
| 5,376,070 A | 12/1994 | Purvis et al. |
| 5,378,231 A | 1/1995 | Johnson et al. |
| 5,382,232 A | 1/1995 | Hague et al. |
| 5,383,231 A | 1/1995 | Yamagishi |
| 5,383,858 A | 1/1995 | Reilly et al. |
| 5,385,540 A | 1/1995 | Abbott et al. |
| 5,388,139 A | 2/1995 | Beland |
| 5,392,849 A | 2/1995 | Matsunaga et al. |
| 5,400,792 A | 3/1995 | Hoebel et al. |
| 5,417,213 A | 5/1995 | Prince |
| 5,431,627 A | 7/1995 | Pastrone et al. |
| 5,433,704 A | 7/1995 | Ross et al. |
| 5,445,621 A | 8/1995 | Poli et al. |
| 5,450,847 A | 9/1995 | Kaempfe et al. |
| 5,453,639 A | 9/1995 | Cronin et al. |
| 5,456,255 A | 10/1995 | Abe et al. |
| 5,458,128 A | 10/1995 | Polanyi et al. |
| 5,459,769 A | 10/1995 | Brown |
| 5,460,609 A | 10/1995 | O'Donnell |
| 5,464,391 A | 11/1995 | Devale |
| 5,468,240 A | 11/1995 | Gentelia et al. |
| 5,469,769 A | 11/1995 | Sawada et al. |
| 5,469,849 A | 11/1995 | Sasaki et al. |
| 5,472,403 A | 12/1995 | Cornacchia et al. |
| 5,474,683 A | 12/1995 | Bryant et al. |
| 5,485,831 A | 1/1996 | Holdsworth et al. |
| 5,489,265 A | 2/1996 | Montalvo et al. |
| 5,494,036 A | 2/1996 | Uber, III et al. |
| 5,494,822 A | 2/1996 | Sadri |
| 5,496,273 A | 3/1996 | Pastrone et al. |
| 5,507,412 A | 4/1996 | Ebert et al. |
| 5,515,851 A | 5/1996 | Goldstein |
| 5,522,798 A | 6/1996 | Johnson et al. |
| 5,531,679 A | 7/1996 | Schulman et al. |
| 5,531,697 A | 7/1996 | Olsen et al. |
| 5,533,978 A | 7/1996 | Teirstein |
| 5,544,215 A | 8/1996 | Shroy, Jr. et al. |
| 5,547,470 A | 8/1996 | Johnson et al. |
| 5,552,130 A | 9/1996 | Kraus et al. |
| 5,553,619 A | 9/1996 | Prince |
| 5,560,317 A | 10/1996 | Bunyan et al. |
| 5,566,092 A | 10/1996 | Wang et al. |
| 5,569,181 A | 10/1996 | Heilman et al. |
| 5,569,208 A | 10/1996 | Woelpper et al. |
| 5,573,515 A | 11/1996 | Wilson et al. |
| 5,579,767 A | 12/1996 | Prince |
| 5,583,902 A | 12/1996 | Bae |
| 5,590,654 A | 1/1997 | Prince |
| 5,592,940 A | 1/1997 | Kampfe et al. |

(56) References Cited

U.S. PATENT DOCUMENTS

| | | |
|---|---|---|
| 5,601,086 A | 2/1997 | Pretlow, III et al. |
| 5,611,344 A | 3/1997 | Bernstein et al. |
| 5,616,124 A | 4/1997 | Hague et al. |
| 5,681,285 A | 10/1997 | Ford et al. |
| 5,687,208 A | 11/1997 | Bae et al. |
| 5,687,708 A | 11/1997 | Farnsworth et al. |
| 5,713,358 A | 2/1998 | Mistretta et al. |
| 5,724,976 A | 3/1998 | Mine et al. |
| 5,725,500 A | 3/1998 | Micheler |
| 5,739,508 A | 4/1998 | Uber, III |
| 5,743,266 A | 4/1998 | Levene et al. |
| 5,768,405 A | 6/1998 | Makram-Ebeid |
| 5,796,862 A | 8/1998 | Pawlicki et al. |
| 5,799,649 A | 9/1998 | Prince |
| 5,800,397 A | 9/1998 | Wilson et al. |
| 5,806,519 A | 9/1998 | Evans, III et al. |
| 5,808,203 A | 9/1998 | Nolan, Jr. et al. |
| 5,827,219 A | 10/1998 | Uber, III et al. |
| 5,827,504 A | 10/1998 | Yan et al. |
| 5,840,026 A | 11/1998 | Uber, III et al. |
| 5,843,037 A | 12/1998 | Uber, III |
| 5,846,517 A | 12/1998 | Unger |
| 5,865,744 A | 2/1999 | Lemelson |
| 5,873,861 A | 2/1999 | Hitchins et al. |
| 5,881,124 A | 3/1999 | Giger et al. |
| 5,882,343 A | 3/1999 | Wilson et al. |
| 5,902,054 A | 5/1999 | Coudray |
| 5,903,454 A | 5/1999 | Hoffberg et al. |
| 5,916,165 A | 6/1999 | Duchon et al. |
| 5,920,054 A | 7/1999 | Uber, III |
| 5,947,935 A | 9/1999 | Kazousky et al. |
| 5,987,347 A | 11/1999 | Khoury et al. |
| 5,988,587 A | 11/1999 | Duchon et al. |
| 6,046,225 A | 4/2000 | Maddock |
| 6,055,985 A | 5/2000 | Bae et al. |
| 6,056,902 A | 5/2000 | Hettinga |
| 6,063,052 A | 5/2000 | Uber, III et al. |
| 6,073,042 A | 6/2000 | Simonetti |
| 6,099,502 A | 8/2000 | Duchon et al. |
| 6,113,568 A | 9/2000 | Olaussen |
| 6,132,396 A | 10/2000 | Antanavich et al. |
| 6,149,627 A | 11/2000 | Uber, III |
| 6,186,146 B1 | 2/2001 | Glickman |
| 6,201,889 B1 | 3/2001 | Vannah |
| 6,221,045 B1 | 4/2001 | Duchon et al. |
| 6,236,706 B1 | 5/2001 | Hsieh |
| 6,248,093 B1 | 6/2001 | Moberg |
| 6,306,117 B1 | 10/2001 | Uber, III |
| 6,313,131 B1 | 11/2001 | Lawyer |
| 6,317,623 B1 | 11/2001 | Griffiths et al. |
| 6,322,535 B1 | 11/2001 | Hitchins et al. |
| 6,344,030 B1 | 2/2002 | Duchon et al. |
| 6,381,486 B1 | 4/2002 | Mistretta et al. |
| 6,387,098 B1 | 5/2002 | Cole et al. |
| 6,397,093 B1 | 5/2002 | Aldrich |
| 6,397,097 B1 | 5/2002 | Requardt |
| 6,402,697 B1 | 6/2002 | Calkins et al. |
| 6,423,719 B1 | 7/2002 | Lawyer |
| 6,442,418 B1 | 8/2002 | Evans, III et al. |
| 6,470,889 B1 | 10/2002 | Bae et al. |
| 6,471,674 B1 | 10/2002 | Emig et al. |
| 6,478,735 B1 | 11/2002 | Pope et al. |
| 6,503,226 B1 | 1/2003 | Martinell et al. |
| 6,520,930 B2 | 2/2003 | Critchlow et al. |
| 6,527,718 B1 | 3/2003 | Connor et al. |
| 6,554,819 B2 | 4/2003 | Reich |
| 6,556,695 B1 | 4/2003 | Packer et al. |
| 6,572,851 B2 | 6/2003 | Muramatsu et al. |
| 6,574,496 B1 | 6/2003 | Golman et al. |
| 6,575,930 B1 | 6/2003 | Trombley, III et al. |
| 6,597,938 B2 | 7/2003 | Liu |
| 6,626,862 B1 | 9/2003 | Duchon et al. |
| 6,635,030 B1 | 10/2003 | Bae et al. |
| 6,643,537 B1 | 11/2003 | Zatezalo et al. |
| 6,652,489 B2 | 11/2003 | Trocki et al. |
| 6,656,157 B1 | 12/2003 | Duchon et al. |
| 6,673,033 B1 | 1/2004 | Sciulli et al. |
| 6,685,733 B1 | 2/2004 | Dae et al. |
| 6,691,047 B1 | 2/2004 | Fredericks |
| 6,699,219 B2 | 3/2004 | Emig et al. |
| 6,731,971 B2 | 5/2004 | Evans et al. |
| 6,754,521 B2 | 6/2004 | Prince |
| 6,775,764 B1 | 8/2004 | Batcher |
| 6,776,764 B2 | 8/2004 | Pinsky |
| 6,866,653 B2 | 3/2005 | Bae |
| 6,876,720 B2 | 4/2005 | Tsuyuki |
| 6,879,853 B2 | 4/2005 | Meaney et al. |
| 6,983,590 B2 | 1/2006 | Roelle et al. |
| 7,094,216 B2 | 8/2006 | Trombley, III et al. |
| 7,267,666 B1 | 9/2007 | Duchon et al. |
| 7,267,667 B2 | 9/2007 | Houde et al. |
| 7,292,720 B2 | 11/2007 | Horger et al. |
| 7,351,221 B2 | 4/2008 | Trombley, III et al. |
| 7,553,294 B2 | 6/2009 | Lazzaro et al. |
| 7,553,295 B2 | 6/2009 | Susi |
| 7,563,249 B2 | 7/2009 | Schriver et al. |
| 7,666,169 B2 | 2/2010 | Cowan et al. |
| 7,688,057 B2 | 3/2010 | Foss et al. |
| 7,861,893 B2 | 1/2011 | Voegele et al. |
| 7,925,330 B2 | 4/2011 | Kalafut et al. |
| 8,007,487 B2 | 8/2011 | Patrick et al. |
| 8,147,464 B2 | 4/2012 | Spohn et al. |
| 8,162,903 B2 | 4/2012 | Reilly et al. |
| 8,295,914 B2 | 10/2012 | Kalafut et al. |
| 8,337,456 B2 | 12/2012 | Schriver et al. |
| 8,377,003 B2 | 2/2013 | Wagner |
| 8,403,909 B2 | 3/2013 | Spohn et al. |
| 8,439,863 B2 | 5/2013 | Fago et al. |
| 8,486,017 B2 | 7/2013 | Masuda et al. |
| 8,905,969 B2 | 12/2014 | Nystrom et al. |
| 8,945,051 B2 | 2/2015 | Schriver et al. |
| 9,101,708 B2 | 8/2015 | Small et al. |
| 9,173,995 B1 | 11/2015 | Tucker et al. |
| 9,199,033 B1 | 12/2015 | Cowan et al. |
| 9,238,099 B2 | 1/2016 | Kalafut et al. |
| 9,242,083 B2 | 1/2016 | Fago et al. |
| 9,259,527 B2 | 2/2016 | Spohn et al. |
| 9,314,749 B2 | 4/2016 | Yagi et al. |
| 9,333,293 B2 | 5/2016 | Williams, Jr. et al. |
| 9,474,857 B2 | 10/2016 | Riley et al. |
| 9,480,788 B2 | 11/2016 | Wagner |
| 9,480,791 B2 | 11/2016 | Reilly |
| 9,555,379 B2 | 1/2017 | Schriver et al. |
| 9,861,752 B2 | 1/2018 | Buder et al. |
| 9,901,671 B2 | 2/2018 | Toews et al. |
| 9,987,413 B2 | 6/2018 | Seibold et al. |
| 10,041,483 B2 | 8/2018 | Chappel et al. |
| 10,112,008 B2 | 10/2018 | Neftel et al. |
| 10,201,666 B2 | 2/2019 | Cowan et al. |
| D847,985 S | 5/2019 | Neff et al. |
| 10,391,234 B2 | 8/2019 | Sams et al. |
| 10,549,084 B2 | 2/2020 | Sokolov et al. |
| 2001/0018937 A1 | 9/2001 | Nemoto |
| 2001/0027265 A1 | 10/2001 | Prince |
| 2001/0056233 A1 | 12/2001 | Uber et al. |
| 2002/0007116 A1 | 1/2002 | Zatezalo et al. |
| 2002/0010551 A1 | 1/2002 | Wang et al. |
| 2002/0026148 A1 | 2/2002 | Uber et al. |
| 2002/0099254 A1 | 7/2002 | Movahed |
| 2002/0123702 A1 | 9/2002 | Cho |
| 2002/0151854 A1 | 10/2002 | Duchon et al. |
| 2003/0050556 A1 | 3/2003 | Uber et al. |
| 2003/0120171 A1 | 6/2003 | Diamantopoulos et al. |
| 2003/0195462 A1 | 10/2003 | Mann et al. |
| 2003/0212364 A1 | 11/2003 | Mann et al. |
| 2003/0216683 A1 | 11/2003 | Shekalim |
| 2003/0226539 A1 | 12/2003 | Kim et al. |
| 2004/0011740 A1 | 1/2004 | Bernard et al. |
| 2004/0025452 A1 | 2/2004 | McLean |
| 2004/0044302 A1 | 3/2004 | Bernard et al. |
| 2004/0064041 A1 | 4/2004 | Lazzaro et al. |
| 2004/0092905 A1 | 5/2004 | Azzolini |
| 2004/0097806 A1 | 5/2004 | Hunter et al. |
| 2004/0154788 A1 | 8/2004 | Symonds |

(56) References Cited

U.S. PATENT DOCUMENTS

| | | |
|---|---|---|
| 2004/0162484 A1 | 8/2004 | Nemoto |
| 2004/0163655 A1 | 8/2004 | Gelfand et al. |
| 2004/0167415 A1 | 8/2004 | Gelfand et al. |
| 2004/0215144 A1 | 10/2004 | Duchon et al. |
| 2004/0253183 A1 | 12/2004 | Uber, III et al. |
| 2004/0254533 A1 | 12/2004 | Schriver et al. |
| 2005/0107697 A1 | 5/2005 | Berke et al. |
| 2005/0171487 A1 | 8/2005 | Haury et al. |
| 2005/0234407 A1 | 10/2005 | Spohn et al. |
| 2005/0234428 A1 | 10/2005 | Spohn et al. |
| 2006/0052794 A1 | 3/2006 | McGill et al. |
| 2006/0079765 A1 | 4/2006 | Neer et al. |
| 2006/0079843 A1 | 4/2006 | Brooks et al. |
| 2006/0167415 A1 | 7/2006 | Nemoto |
| 2007/0068964 A1 | 3/2007 | Tanaami et al. |
| 2007/0129705 A1 | 6/2007 | Trombley, III et al. |
| 2007/0161970 A1 | 7/2007 | Spohn et al. |
| 2007/0219496 A1 | 9/2007 | Kamen et al. |
| 2007/0276327 A1 | 11/2007 | Kalafut et al. |
| 2008/0015406 A1 | 1/2008 | Dlugos et al. |
| 2008/0045925 A1 | 2/2008 | Stepovich et al. |
| 2008/0086087 A1 | 4/2008 | Spohn et al. |
| 2008/0167621 A1 | 7/2008 | Wagner et al. |
| 2008/0183131 A1 | 7/2008 | Duchon et al. |
| 2009/0112164 A1 | 4/2009 | Reilly et al. |
| 2009/0216192 A1 | 8/2009 | Schriver et al. |
| 2009/0234226 A1 | 9/2009 | Nemoto |
| 2009/0247865 A1 | 10/2009 | Spohn et al. |
| 2009/0247961 A1 | 10/2009 | Carlyon |
| 2009/0312744 A1 | 12/2009 | Keeley et al. |
| 2010/0130809 A1 | 5/2010 | Morello |
| 2010/0222768 A1* | 9/2010 | Spohn ............... A61M 5/1452 604/506 |
| 2010/0249586 A1 | 9/2010 | Cocker et al. |
| 2010/0262078 A1 | 10/2010 | Blomquist |
| 2010/0331779 A1 | 12/2010 | Nystrom et al. |
| 2011/0275988 A1 | 11/2011 | Davis et al. |
| 2012/0089114 A1 | 4/2012 | Hemond et al. |
| 2012/0101472 A1 | 4/2012 | Schroeder et al. |
| 2012/0123229 A1* | 5/2012 | Butterfield ........ A61M 5/16859 600/561 |
| 2012/0178629 A1 | 7/2012 | Hudson et al. |
| 2012/0203177 A1 | 8/2012 | Lanier, Jr. et al. |
| 2012/0204997 A1 | 8/2012 | Winn et al. |
| 2012/0217231 A1 | 8/2012 | Moore et al. |
| 2012/0245560 A1 | 9/2012 | Hochman |
| 2013/0030290 A1 | 1/2013 | Nemoto |
| 2013/0123619 A1 | 5/2013 | Griggs |
| 2013/0245439 A1 | 9/2013 | Small et al. |
| 2013/0245604 A1 | 9/2013 | Kouyoumjian et al. |
| 2013/0261993 A1 | 10/2013 | Ruchti et al. |
| 2014/0027009 A1 | 1/2014 | Riley et al. |
| 2014/0142537 A1 | 5/2014 | Gibson et al. |
| 2014/0276550 A1 | 9/2014 | Uram et al. |
| 2016/0030662 A1 | 2/2016 | Uber, III et al. |
| 2016/0278725 A1 | 9/2016 | Van Nijnatten |
| 2016/0331896 A1 | 11/2016 | Nemoto et al. |
| 2017/0035974 A1 | 2/2017 | Berry et al. |
| 2017/0056603 A1 | 3/2017 | Cowan et al. |
| 2017/0143898 A1 | 5/2017 | Grosse-Wentrup et al. |
| 2017/0258982 A1 | 9/2017 | Kemper |
| 2017/0290971 A1 | 10/2017 | Hedmann et al. |
| 2017/0343446 A1 | 11/2017 | Ciolkosz et al. |
| 2018/0133392 A1 | 5/2018 | Dembo et al. |
| 2019/0083699 A1 | 3/2019 | Spohn et al. |

FOREIGN PATENT DOCUMENTS

| | | |
|---|---|---|
| CA | 2234050 A1 | 4/1997 |
| CN | 1671428 A | 9/2005 |
| CN | 103347552 A | 10/2013 |
| DE | 3203594 A1 | 8/1983 |
| DE | 3726452 A1 | 2/1989 |
| DE | 4426387 A1 | 8/1995 |
| DE | 19702896 A1 | 7/1997 |
| DE | 19647701 A1 | 5/1998 |
| DE | 19919572 A1 | 11/2000 |
| EP | 0121216 A1 | 10/1984 |
| EP | 0129910 A1 | 1/1985 |
| EP | 0189491 A1 | 8/1986 |
| EP | 0192786 A2 | 9/1986 |
| EP | 0245160 A1 | 11/1987 |
| EP | 0319275 A1 | 6/1989 |
| EP | 0337924 A2 | 10/1989 |
| EP | 0343501 A2 | 11/1989 |
| EP | 0364966 A1 | 4/1990 |
| EP | 0365301 A1 | 4/1990 |
| EP | 0372152 A1 | 6/1990 |
| EP | 0378896 A2 | 7/1990 |
| EP | 0429191 A2 | 5/1991 |
| EP | 0471455 A2 | 2/1992 |
| EP | 0475563 A1 | 3/1992 |
| EP | 0595474 A2 | 5/1994 |
| EP | 0600448 A2 | 6/1994 |
| EP | 0619122 A1 | 10/1994 |
| EP | 0439711 B1 | 5/1995 |
| EP | 0869738 A1 | 10/1998 |
| EP | 1016427 A2 | 7/2000 |
| EP | 2990073 A1 | 3/2016 |
| FR | 2493708 A1 | 5/1982 |
| FR | 2561949 A1 | 10/1985 |
| GB | 201800 A | 8/1923 |
| GB | 2252656 A | 8/1992 |
| GB | 2328745 A | 3/1999 |
| JP | S5017781 A | 2/1975 |
| JP | S5815842 A | 1/1983 |
| JP | S59214432 A | 12/1984 |
| JP | S60194934 A | 10/1985 |
| JP | S60194935 A | 10/1985 |
| JP | S60253197 A | 12/1985 |
| JP | S62216199 A | 9/1987 |
| JP | S6340538 A | 2/1988 |
| JP | S63290547 A | 11/1988 |
| JP | H01207038 A | 8/1989 |
| JP | H02224647 A | 9/1990 |
| JP | H02234747 A | 9/1990 |
| JP | H0355040 A | 3/1991 |
| JP | H04115677 A | 4/1992 |
| JP | H0584296 A | 4/1993 |
| JP | H07178169 A | 7/1995 |
| JP | H0849598 A | 2/1996 |
| JP | H0999034 A | 4/1997 |
| JP | H10211198 A | 8/1998 |
| JP | 2000175900 A | 6/2000 |
| JP | 2003102724 A | 4/2003 |
| JP | 2003116843 A | 4/2003 |
| JP | 2003210456 A | 7/2003 |
| JP | 2003225234 A | 8/2003 |
| JP | 2004174008 A | 6/2004 |
| JP | 2004236849 A | 8/2004 |
| JP | 2004298550 A | 10/2004 |
| JP | 4960180 B2 | 6/2012 |
| JP | 5063593 B2 | 10/2012 |
| JP | 5203971 B2 | 6/2013 |
| JP | 5227791 B2 | 7/2013 |
| JP | 5490840 B2 | 5/2014 |
| WO | 8001754 A1 | 9/1980 |
| WO | 8500292 A1 | 1/1985 |
| WO | 8803815 A1 | 6/1988 |
| WO | 9114232 A1 | 9/1991 |
| WO | 9114233 A1 | 9/1991 |
| WO | 9315658 A1 | 8/1993 |
| WO | 9325141 A1 | 12/1993 |
| WO | 9415664 A1 | 7/1994 |
| WO | 9632975 A1 | 10/1996 |
| WO | 9712550 A1 | 4/1997 |
| WO | 9820919 A1 | 5/1998 |
| WO | 9924095 A2 | 5/1999 |
| WO | 0061216 A1 | 10/2000 |
| WO | 0141835 A2 | 6/2001 |
| WO | 03015633 A1 | 2/2003 |
| WO | 2004012787 A2 | 2/2004 |
| WO | 2004035116 A1 | 4/2004 |

(56) References Cited

FOREIGN PATENT DOCUMENTS

| | | | |
|---|---|---|---|
| WO | 2004091688 A2 | 10/2004 | |
| WO | 2005016165 A1 | 2/2005 | |
| WO | 2005035995 A1 | 4/2005 | |
| WO | 2006042093 A1 | 4/2006 | |
| WO | 2007079016 A2 | 7/2007 | |
| WO | 2007092618 A2 | 8/2007 | |
| WO | 2007116840 A1 | 10/2007 | |
| WO | 2007116862 A1 | 10/2007 | |
| WO | 2007116891 A1 | 10/2007 | |
| WO | 2007133942 A2 | 11/2007 | |
| WO | 2008078604 A1 | 7/2008 | |
| WO | 2008106108 A1 | 9/2008 | |
| WO | 2009051995 A1 | 4/2009 | |
| WO | WO-2009051995 A1 * | 4/2009 | ........ A61M 5/14212 |
| WO | 2010027636 A1 | 3/2010 | |
| WO | 2010117841 A1 | 10/2010 | |
| WO | 2011002744 A1 | 1/2011 | |
| WO | 2011011346 A1 | 1/2011 | |
| WO | 2011097487 A2 | 8/2011 | |
| WO | 2011125303 A1 | 10/2011 | |
| WO | 2012048277 A2 | 4/2012 | |
| WO | 2012155035 A1 | 11/2012 | |
| WO | 2013043868 A1 | 3/2013 | |
| WO | 2014144651 A2 | 9/2014 | |
| WO | 2014179326 A1 | 11/2014 | |
| WO | 2014190264 A1 | 11/2014 | |
| WO | 2015106107 A1 | 7/2015 | |
| WO | 2015164783 A1 | 10/2015 | |
| WO | 2016112163 A1 | 7/2016 | |
| WO | 2016172467 A1 | 10/2016 | |
| WO | 2016191485 A1 | 12/2016 | |
| WO | 2017012781 A1 | 1/2017 | |
| WO | 2017038575 A1 | 3/2017 | |
| WO | 2017096072 A1 | 6/2017 | |
| WO | 2017152036 A1 | 9/2017 | |
| WO | 2018060505 A1 | 4/2018 | |
| WO | 2018075386 A1 | 4/2018 | |
| WO | 2018089882 A1 | 5/2018 | |

OTHER PUBLICATIONS

Awai, K., et al., "Effect of contrast material injection duration and rate on aortic peak time and peak enhancement at dynamic CT involving injection protocol with dose tailored to patient weight," Radiology, vol. 230, Issue 1, pp. 142-150, 2004.
Bae, et al. "Aortic and Hepatic Contrast Medium Enhancement at CT—Part I, Prediction with a Computer Model", Radiology 1998;207:647-655.
Bae, K.T., et al., "Multiphasic Injection Method for Uniform Prolonged Vascular Enhancement at CT Angiography: Pharmacokinetic Analysis and Experimental Porcine Model," Radiology, vol. 216, Issue 3, pp. 872-880 (Sep. 2000).
Bae, K.T. et al., "Peak Contrast Enhancement in CT and MR Angiography: When Does it Occur and Why? Pharmacokinetic Study in a Porcine Model", Radiology, vol. 227, Jun. 2003, pp. 809-816.
Bae, K.T., et al., "Uniform vascular contrast enhancement and reduced contrast medium volume achieved by using exponentially decelerated contrast material injection method," Radiology, vol. 231, Issue 3, pp. 732-736, 2004.
Baker, Aaron; et al. "Fluid Mechanics Analysis of a Spring-Loaded Jet Injector." IEEE Transactions on Biomedical Engineering, vol. 46, No. 2, Feb. 1999.
Becker, C.R., et al., "Optimal contrast application for cardiac 4-detector-row computed tomography," Investigative Radiology, vol. 38, Issue 11, pp. 690-694 (Nov. 2003).
Blomley, M.J.K. and Dawson, P., "Bolus Dynamics: Theoretical and Experimental Aspects," The Brit. J. of Radiology, vol. 70, No. 832, pp. 351-359 (Apr. 1997).
Brunette J.; et al., "Comparative rheology of low- and iso-osmolarity contrast agents at different temperature", Catheterization and Cardiovascular Interventions, 2008, vol. 71 Issue No. 1, 78-83.

Cademartiri, F. and Luccichenti, G., et al. "Sixteen-row multislice computed tomography: basic concepts, protocols, and enhanced clinical applications," Seminars in Ultrasound, CT and MRI, vol. 25, Issue 1, pp. 2-16, 2004.
Dardik, H. et al., "Remote Hydraulic Syringe Actuator," Arch. Surg., vol. 115, Issue 1, Jan. 1980.
Dawson, P. and Blomley, M., "The value of mathematical modelling in understanding contrast enhancement in CT with particular reference to the detection of hypovascular liver metastases," European Journal of Radiology, vol. 41, Issue 3, pp. 222-236 (Mar. 2002).
"Digital Injector for Angiography", Sias. (Sep. 7, 1993).
Disposable Low-Cost Catheter Tip Sensor Measures Blood Pressure during Surgery, Sensor (Jul. 1989).
EZ Chem Brochure, E-Z-EM, Inc. (Jul. 2007).
Fisher, M E. and Teo, K.I., "Optimal insulin infusion resulting from a mathematical model of blood glucose dynamics", IEEE Transactions on Biomedical Engineering, vol. 36, Issue 4, pp. 479-486, 1989.
Flegal, K.M., et al., "Prevalence and trends in obesity among US adults," JAMA, 2002, vol. 288, Issue 14, pp. 1-4, (1999-2000).
Fleischmann, D. and Hittmair, K., "Mathematical analysis of arterial enhancement and optimization of bolus geometry for CT angiography using the discrete Fourier transform," Journal of Computer Assisted Tomography, vol. 23, Issue 3, pp. 474-484 (May/Jun. 1999).
Fleischmann, D., "Contrast Medium Injection Technique," In: U. Joseph Schoepf: "Multidetector—Row CT of The Thorax," pp. 47-59 (Jan. 22, 2004).
Fleischmann, D., "Present and Future Trends in Multiple Detector—Row CT Applications; CT Angiography", European Radiology, vol. 12, Issue 2, Supplement 2, Jul. 2002, pp. s11-s15.
Gardiner, G. A., et al., "Selective Coronary Angiography Using a Power Injector," AJR Am J Roentgenol., vol. 146, Issue 4, pp. 831-833 (Apr. 1986).
Garrett, J. S., et al., "Measurement of cardiac output by cine computed tomography," The American Journal of Cardiology, vol. 56, Issue 10, pp. 657-661, 1985.
Gembicki, F.W., "Vector Optimization for Control with Performance and Parameter Sensitivity Indices," PhD Thesis Case Western Reserve University, 1974.
Gentilini A., et al., "A new paradigm for the closed-loop intraoperative administration of analgesics in humans," IEEE Transactions on Biomedical Engineering, vol. 49, Issue 4, pp. 289-299 (Apr. 2002).
Gerlowski L.E. and Jain R.K., "Physiologically Based Pharmacokinetic Modeling: Principles and Applications," Journal of Pharmaceutical Sciences, vol. 72, pp. 1104-1125, Oct. 1983.
Goss, J. E., et al., "Power injection of contrast media during percutaneous transluminal coronary artery angioplasty," Catheterization and Cardiovascular Diagnosis, vol. 16, Issue 3, pp. 195-198 (Mar. 1989).
Grant, S.C.D. et al., "Reduction of Radiation Exposure to the Cardiologist during Coronary Angiography by the Use of a Remotely Controlled Mechanical Pump for Injection of Contrast Medium," Catheterization and Cardiovascular Diagnosis, vol. 25, Issue 2, pp. 107-109 (Feb. 1992).
Hackstein, N. et al., "Glomerular Filtration Rate Measured by Using Triphasic Helical CT with a Two-Point Patlak Plot Technique," Radiology, vol. 230, Issue 1, pp. 221-226, Jan. 2004.
Hansen, P.C, Regularization tools: a MATLAB package for analysis and solution of discrete ill-posed problems, Numerical Algorithms, vol. 6, Issue 1, pp. 35, 1994.
Hansen, P.C., "The truncated SVD as a method for regularization," BIT Numerical Mathematics, vol. 27, Issue 4, pp. 534-555, 1987.
Harris P., H. D. "The Human Pulmonary Circulation," Edinburgh, Churchill Livingstone, (Appendix I), 1986.
Hayes, M., "Statistical Digital Signal Processing and Modeling", New York, New York, Wiley and Sons, 1996, pp. 154-177, (Prony's method).
Heiken; J.P. et al., "Dynamic Contrast-Enhanced CT of the Liver: Comparison of Contrast Medium Injection Rates and Uniphasicand Biphasic Injection Protocols", Radiology, May 1993, vol. 187, No. 2, pp. 327-331.

(56) References Cited

OTHER PUBLICATIONS

"Infus O.R. Multi-Drug Syringe Pump with Smart Labels," Bard MedSystems Division Inc., pp. 2693-2696 (2005).
"International Preliminary Report on Patentability from PCT Application No. PCT/US2018/048284", dated Mar. 12, 2020.
Ireland, M.A., et al., "Safety and Convenience of a Mechanical Injector Pump for Coronary Angiography," Catheterization and Cardiovascular Diagnosis, vol. 16, Issue 3, pp. 199-201 (1989).
Jacobs, J.R., "Algorithm for optimal linear model-based control with application to pharmacokinetic model-driven drug delivery," IEEE Transactions on Biomedical Engineering, vol. 37, Issue 1, pp. 107-109 (Jan. 1990).
Korosec, F.R., "Physical Principles of Phase-Contrast, Time-of-Flight, and Contrast-Enhanced MR Angiography," 41st Annual Meeting of American Association of Physicists in Medicine, Jul. 25-29, 1999.
Korosec, Frank, "Basic Principles of Phase-contrast, Time-of-flight, and Contrast-enhanced MR Angiography", 1999.
Krause, W, "Application of pharmacokinetics to computed tomography: injection rates and schemes: mono-, bi-, or multiphasic?," Investigative Radiology, vol. 31, Issue 2, pp. 91-100, Feb. 1996.
Krieger, R. A., "CO2-Power-Assisted Hand-Held Syringe: Better Visualization during Diagnostic and InterventionalAngiography," Cathet Cardiovasc Diagn., vol. 19, Issue 2, pp. 123-128 (Feb. 1990).
Liebel-Flarsheim Company, "Angiomat 6000 Digital Injection System-Operator's Manual", Document No. 600950, Rev. 1, Jan. 1990.
Mahnken, A. H., et al., "Determination of cardiac output with multislice spiral computed tomography: a validation study," Investigative Radiology, vol. 39, Issue 8, pp. 451-454, Aug. 2004.
Mahnken, A. H., et al., "Measurement of cardiac output from a test-bolus injection in multislice computed tomography," European Radiology, vol. 13, Issue 11, pp. 2498-2504, 2003.
Mark V/Mark V Plus Injector Operation Manual KMP 805P Rev. B. Medrad, Inc, 1990.
McClellan, J.H., "Parametric Signal Modeling," Chapter 1 in Advanced Topics in Signal Processing, Pentice-Hall, Englewood Cliffs, NJ (1988).
MCT and MCT Plus Injection Systems Operation Manual KMP 810P, Medrad, Inc, 1991.
Morden Peter.; et al., "The Role of Saline Flush Injection Rate in Displacement of CT Injectable Peripherally Inserted Central Catheter Tip During Power Injection of Contrast Material", AJR, Jan. 2014, 202, W13-W18.
Neatpisarnvanit, C. and Boston, J.R., "Estimation of plasma insulin from plasma glucose", IEEE Transactions on Biomedical Engineering, vol. 49, Issue 11, pp. 1253-1259, 2002.
SWISS; Medical Care., "CT Expres Contrast Media Delivery System Operation Manual Rev 1", 2004.
Angiography, Catheterization and Cardiovascular Diagnosis, vol. 19, pp. 123-128, 1990.
Awai Kazuo; et al., "Aortic and Hepatic Enhancement and Tumor-to-Liver Contrast: Analysis of the Effect of Different Concentrations of Contrast Material at Multi-Detector Row Helical CT.", Radiology, 2002, vol. 224; Issue 3., 757-763.
Ostergaard, L., et al., "High resolution measurement of cerebral blood flow using intravascular tracer boluspassages. Part 1: Mathematical approach and statistical analysis," Magnetic Resonance in Medicine, vol. 36, Issue 5,pp. 715-725 (Nov. 1996).
Ostergaard, L., et al., "High resolution measurement of cerebral blood flow using intravascular tracer boluspassages. Part II: Experimental comparison and preliminary results," Magn Reson Med, vol. 36, Issue 5, pp. 726-736(Nov. 1996).
Parker, K.J., et al., "A Particulate Contrast Agent With Potential for Ultrasound Imaging of Liver," Ultrasound in Medicine & Biology, vol. 13, Issue 9, pp. 555-566 (Sep. 1987).
Rosen, B.R. et al., "Perfusion Imaging with NMR Contrast Agents," Magentic Resonance in Medicine, vol. 14, No. 2, pp. 249-265, May 1, 1990.
Sablayrolles, J-L, "Cardiac CT: Experience from Daily Practice", Advance CT, A GE Healthcare Publication. Aug. 2004.
Stevens, M.A., et al. "A Prospective Randomized Trial of Prevention Measures in Patients at High Risk for Contrast Nephropathy," J. of the ACC, vol. 33, Issue 2, pp. 403-411, Feb. 1999.
"The Solution for Your IV Formulas", Valley Lab. Inc., E-39-15, 3399, 3400, 2646.
Wada D.R. and Ward; D.S., "The hybrid model: a new pharmacokinetic model for computer-controlled infusion pumps", IEEE Transactions on Biomedical Engineering, 1994, vol. 41, Issue 2, pp. 134-142.
Wada, D.R. and Ward, D.S., "Open loop control of multiple drug effects in anesthesia", IEEE Transactions on Biomedical Engineering, vol. 42, Issue 7, pp. 666-677, 1995.
Yamashita, Y. et al., "Abdominal Helical CT: Evaluation of Optimal Doses of Intravenous Contrast Material—A Prospective Randomized Study," Radiology, vol. 216, Issue 3, pp. 718-723, Sep. 1, 2000.

\* cited by examiner

SYSTEM AND METHOD FOR DRIVE MEMBER POSITION AND FLUID INJECTOR SYSTEM MECHANICAL CALIBRATION

CROSS REFERENCE TO RELATED APPLICATIONS

This application is a § U.S. national phase application under 35 U.S.C. § 371 of PCT International Application No. PCT/US2018/048284, filed 28 Aug. 2018 and claims priority to U.S. Provisional Application No. 62/552,427, titled "System and Method for Drive Member Position Calibration", filed on 31 Aug. 2017, and U.S. Provisional Application No. 62/552,589, titled "System and Method for Characterizing and Correcting Fluid Injector System Slack", filed on 31 Aug. 2017, the disclosures of which are incorporated herein in their entirety.

BACKGROUND OF THE DISCLOSURE

Field of the Disclosure

The present disclosure relates generally to a system and method for calibrating a fluid injector, such as a medical fluid injector, and further, to a system and method for drive member position calibration of the fluid injector and characterization and correcting for mechanical slack in fluid injector systems.

Description of Related Art

In many medical diagnostic and therapeutic procedures, a medical practitioner, such as a physician, injects a patient with one or more medical fluids. In recent years, a number of fluid delivery systems having injector-actuated syringes and fluid injectors for pressurized injection of fluids, such as a contrast solution (often referred to simply as "contrast"), a flushing agent, such as saline, and other medical fluids have been developed for use in procedures such as angiography, computed tomography (CT), ultrasound, magnetic resonance imaging (MRI), positron emission tomography (PET), and other imaging procedures. In general, these fluid delivery systems are designed to deliver a preset amount of fluid at a desired flow rate.

An actual flow rate (or delivered volume) of fluid that is delivered to the patient is targeted to be as close as possible to the desired flow rate (or desired volume). However, the actual performance of the fluid delivery system is a function of many factors due to overall impedance and capacitance of the fluid delivery system. In certain delivery procedures, impedance and capacitance of the fluid delivery system may cause a fluid flow over-rate or under-rate (or volume over- or under-delivery) from a desired flow rate (or desired volume).

Accordingly, there is a need in the art for improved calibration of the fluid injector to better ensure that a desired volume of fluid is accurately delivered to a patient at a desired flow rate. There is a further need for improved systems and methods for calibrating a fluid injector, as well as systems and methods for characterizing the performance of a fluid delivery system and correlating the desired performance with actual performance in terms of fluid flow rate and volume delivered.

SUMMARY OF DISCLOSURE

In some examples of the present disclosure, an improved method for calibrating the zero position of the drive member of an injector system is disclosed. In examples, according to the present disclosure, an automated method of position calibration of the drive member of a fluid injector is disclosed. This method addresses sources of error in positional accuracy, such as disposable syringe tolerance and injector wear over time. According to other embodiments of the present disclosure, methods and fluid injector systems for determining and correcting for the amount of slack in a fluid injection apparatus are described. An understanding of the calibration and the amount of slack in a fluid injection system allows a processor to correct for the slack, thereby ensuring more accurate fluid delivery to the patient and more accurate imaging processes.

In one embodiment according to the present disclosure, the position of the drive member of the fluid injector system may be calibrated according to the following steps. At least one disposable syringe comprising a drive member is inserted in a syringe port and an injector piston is operably connected to the drive member. The drive member is driven distally from a proximal position in the syringe body, until it contacts the distal end of the interior of the syringe, and cannot travel further or a specified level or magnitude of resistance is detected. The drive member continues to be driven distally until a load force value on the distal end of the syringe is reached. The force on the drive member slowly is decreased until the load force value reaches zero or a predetermined load force value. The position of the drive member is recorded as the zero volume position for that syringe. The zero position may be recorded and saved by the injector for each individual syringe, such as by recording the zero position by a processor within its memory, and then used during injection protocols utilizing that syringe to more accurately deliver a desired fluid volume and/or flow rate.

In another embodiment of the present disclosure, the position of the drive member of the fluid injector system may be calibrated according to the following steps. At least one disposable syringe comprising a drive member is inserted in a syringe port and an injector piston is operably connected to the drive member. The drive member is moved proximally from a distal position in the syringe body thereby drawing a vacuum load, until it reaches a predetermined vacuum load. The force on the drive member may then be released and the drive member may move distally until the vacuum load force value reaches zero or a predetermined vacuum load force value. The position of the drive member is recorded as the zero volume position for that syringe. The zero position may be recorded and saved by the injector for each individual syringe, such as by recording the zero position by a processor within its memory, and then used during injection protocols utilizing that syringe to more accurately deliver a desired fluid volume and/or flow rate.

In embodiments according to the present disclosure, this method may be stored on memory, controlled by a processor, and carried out automatically whenever a new syringe or set of syringes is connected to the injector. According to other examples, this method may be carried out at the prompting of a user or the processor may prompt a user and recommend that the method be carried out.

In other embodiments, a method of the present disclosure may be used to track wear on a syringe if it is applied multiple times, wherein the changes in the zero volume position are tracked over the use-life of the syringe. In other examples, the method of the present disclosure may be used to track wear on the injector components and/or a batch of syringes if applied to the batch of syringes over time, wherein the zero volume positions of the syringes are tracked and changes in the zero volume position is monitored over time. This may have applications in predictive maintenance of the injector, and the syringes.

In other embodiments, a method according to the present disclosure may be used to verify whether a syringe is faulty, for example if the zero volume position is outside of a pre-determined range, wherein the determined range is representative of normal variance within the accepted syringe tolerances. In examples, a zero volume position that is too proximal along the longitudinal axis, relative to the predetermined range, may indicate a fault condition, such as a cocked or misaligned plunger. A zero volume position that is too far distal along the longitudinal axis, relative to the predetermined range, may indicate other problems or fault conditions. Either boundary issue relative to the expected predetermined range may indicate an error or alarm condition to the user with respective notification to the user via a visual and/or audible alert, and in certain conditions may cause the injector to cease injection procedures.

In other embodiments, the method according to the present disclosure may be used to measure recoil of a plunger or a syringe as an indication of wear of injector components or wear of syringe components in a multi-use syringe set.

In other embodiments, the method according to the present disclosure may measure static or dynamic friction of the plunger and/or the interior surface of the syringe body at the beginning of injection procedures, and initial values may be compared to expected, standard values, or measured values over time for a syringe design. Static and/or dynamic friction may be compared to known coefficients of friction of silicone, silicone compounds, and/or mixtures containing silicone to assess the presence or absence of silicone in the plunger and/or syringe. This may provide information on production standards for various production batches of syringes.

In some examples of the present disclosure, a fluid injector system for delivering fluid to a patient includes a fluid injector having a processor and at least one piston, and at least one syringe removably connected to the fluid injector and including a plunger disposed in a barrel of the at least one syringe and reversibly movable along a longitudinal axis of the syringe. The at least one piston of the fluid injector is configured to engage the plunger and travel along the longitudinal axis inside the barrel of the at least one syringe, and at least one valve is in fluid communication with the at least one syringe and at least one fluid container. The valve is switchable between a first position in which the at least one syringe is in fluid communication with the at least one fluid container, a second position in which the at least one syringe is isolated from the at least one fluid container, and a third position where the at least one syringe is in fluid communication with a patient. The processor of the fluid injector is programmed or configured to drive the at least one piston of the fluid injector to a distal end of the at least one syringe, retract the at least one piston toward a proximal end of the at least one syringe to draw fluid into the at least one syringe from the at least one fluid container, measure and store a reference position of the at least one piston within the at least one syringe, switch the at least one valve from the first position to the second position, drive the at least one piston toward the distal end of the at least one syringe until a desired load on the piston is reached, measure and store a contact position of the at least one piston within the at least one syringe, wherein the contact position is a position where the desired load is reached, and derive a slack correction volume based at least partially on the difference between the reference position and the contact position.

In other examples of the present disclosure, the processor of the fluid injector is programmed or configured to switch the at least one valve between the first position and the second position.

In other examples of the present disclosure, the processor of the fluid injector is programmed or configured to relieve pressure in the at least one syringe. In other embodiments, the system may repeatedly determine and store a slack correction volume over a specified time period, for example, at an initial use of the at least one syringe or at the beginning of the day, week, month, or other selected time period. Once repeated measurements have been taken and stored for the slack correction volume over time, the fluid injector, for example the processor, may develop a slack curve for each piston of the injector as a function of time. The injector may then be configured to provide an alert to a user if a measured slack correction volume for at least one piston is significantly different from an expected slack correction volume based on the slack curve for the at least one piston.

In other examples of the present disclosure, a method for characterizing and correcting fluid injection system slack includes: driving at least one drive member of a fluid injector to a distal end of at least one syringe connected to the fluid injector, retracting the at least one drive member toward a proximal end of the at least one syringe to draw fluid into the at least one syringe from at least one fluid container in fluid communication with the at least one syringe, switching at least one valve, which may be a stopcock, from a first position where the at least one syringe is in fluid communication with the at least one fluid container a second position where the at least one syringe is isolated from the at least one fluid container to isolate the at least one syringe from the at least one part of the fluid injection system, measuring and storing a reference position of the at least one drive member within the at least one syringe, driving the at least one drive member toward the distal end of the at least one syringe until a desired load on the at least one drive member is reached, measuring and storing a contact position of the at least one drive member within the at least one syringe, wherein the contact position is a position where the desired load is reached, and deriving a slack correction volume based at least partially on the difference between the reference position and the contact position.

In other examples of the present disclosure, a method for characterizing and correcting fluid injection system slack includes driving at least one drive member of a fluid injector to a distal end of at least one syringe connected to the fluid injector, retracting the at least one drive member toward a proximal end of the at least one syringe to draw fluid into the at least one syringe from at least one fluid container in fluid communication with the at least one syringe, switching at least one valve from a first position where the at least one syringe is in fluid communication with the at least one fluid container to a second position where the at least one syringe is isolated from the at least one fluid container to isolate the at least one syringe from the at least one part of the fluid injection system, driving the at least one drive member toward the distal end of the at least one syringe until a desired load on the at least one drive member is reached, measuring and storing a contact position of the at least one drive member within the at least one syringe, relieving pressure from the at least one syringe until a pressure within the at least one syringe is equal to where the at least one drive member has no applied load, measuring and storing a reference position of the at least one drive member within the at least one syringe where the pressure within the at least one syringe is equal to the pressure applied by the at least one drive member, and deriving a slack correction volume based at least partially on the difference between the reference position and the contact position.

In other examples of the present disclosure, the methods further include evacuating the fluid from the at least one syringe, filling the at least one syringe with a desired volume of fluid plus an additional volume of fluid equal to the slack correction volume, and delivering the fluid from the at least one syringe to a patient.

In other examples of the present disclosure, the method steps are performed at least partially by a processor configured to control a motor driving the drive member of the injector.

In other embodiments, the methods may include the system repeatedly determining and storing a slack correction volume over a specified time period, for example, at an initial use of the at least one syringe or at the beginning of the day, week, month, or other selected time period. Once repeated measurements have been taken and stored by the method for the slack correction volume over time, the method may further include the fluid injector, for example the processor, developing a slack curve for each drive member of the injector as a function of time. In certain embodiments, the method may then include providing an alert to a user if a measured slack correction volume for at least one drive member is significantly different from an expected slack correction volume based on the slack curve for the at least one drive member.

Various other aspects of the system and method for injector position calibration of the fluid injector are disclosed in one or more of the following numbered clauses:

Clause 1. A method for calibrating the position of a drive member of a fluid injector system comprising the steps of: engaging at least one syringe comprising a drive member with at least one piston of a fluid injector such that the at least one piston is in operable communication with the drive member of the at least one syringe; driving the drive member with the at least one piston to a distal-most position in the at least one syringe; applying a first predetermined load force on a distal end of the at least one syringe with the drive member; recording a position of the drive member at which the first predetermined load force is achieved; moving the drive member in a proximal direction at a predetermined rate until a second predetermined load force that is less than the first predetermined load force is achieved; and recording a position of the drive member at which the second predetermined load force is achieved.

Clause 2. A method of clause 1, wherein the drive member comprises a plunger, and wherein the at least one piston drives the plunger.

Clause 3. A method of clause 1, wherein the at least one syringe comprises a rolling diaphragm syringe having a proximal end as the drive member and comprising a piston engagement portion, and wherein the at least one piston releasably engages the piston engagement portion to drive the drive member.

Clause 4. A method of any of clauses 1 to 3, wherein the at least one piston includes a linear actuator.

Clause 5. A method of any of clauses 1 to 4, wherein the at least one piston includes a motor.

Clause 6. A method of any of clauses 1 to 5, further including the step of releasing the load force applied to the drive member at a predetermined rate until the load force value is reduced to zero or a predetermined value.

Clause 7. A method of any of clauses 1 to 5, further including the step of driving the drive member in a proximal direction at a predetermined rate until the load force value is reduced to zero or a predetermined value.

Clause 8. An injection system includes a fluid injector comprising at least one piston, at least one syringe having a drive member, a distal end and configured to contain fluid, at least one piston on the fluid injector and configured to operatively engage the drive member of the at least one syringe; and at least one computing device having memory and a controller in operable communication with the at least one piston, wherein the controller is configured to apply a distal force to the at least one piston to drive the drive member in a distal direction to a distal-most position on the distal end of the at least one syringe, apply a first predetermined load force to the distal end of the at least one syringe with the drive member, move the drive member in a proximal direction until a second predetermined load force that is less than the first predetermined load force is achieved, and store in the memory a position of the drive member at which the second predetermined load force is achieved.

Clause 9. The injection system of clause 8, wherein the drive member comprises a plunger, and wherein the at least one piston is configured to drive the plunger.

Clause 10. The injection system of clause 8 or clause 9, wherein the at least one syringe includes a rolling diaphragm syringe having a proximal end as the drive member and including a piston engagement portion, and wherein the at least one piston releasably engages the piston engagement portion to drive the drive member.

Clause 11. The injection system of any of clauses 8 to 10, wherein the at least one piston includes a linear actuator.

Clause 12. The injection system of any of clauses 8 to 11, wherein the at least one piston includes a motor.

Clause 13. The injection system of any of clauses 8 to 12, wherein the controller is configured to release the load force applied to the drive member at a predetermined rate until the load force value is reduced to zero or a predetermined value.

Clause 14. The injection system of any of clauses 8 to 13, wherein the controller is configured to drive the drive member in a proximal direction at a predetermined rate until the load force value is reduced to zero or a predetermined value.

Clause 15. A fluid injector system for delivering at least one fluid to a patient, the system comprising: a fluid injector having a processor and at least one drive member; at least one syringe removably connected to the fluid injector and comprising a plunger disposed in a barrel of the at least one syringe and reversibly movable along a longitudinal axis of the at least one syringe, wherein the at least one drive member of the fluid injector is configured to engage the plunger and travel along the longitudinal axis inside the barrel of the at least one syringe; and at least one valve in fluid communication with the at least one syringe and at least one fluid container, wherein the valve is switchable between a first position in which the syringe is in fluid communication with the fluid container, a second position in which the at least one syringe is isolated from the fluid container, and a third position where the at least one syringe is in fluid communication with a patient; wherein, the processor of the fluid injector is programmed or configured to: drive the at least one drive member of the fluid injector to a distal end of the at least one syringe; retract the at least one drive member toward a proximal end of the at least one syringe to draw fluid into the at least one syringe from the at least one fluid container; measure and store a reference position of the at least one drive member within the at least one syringe; switch the at least one valve from the first position to the second position; drive the at least one drive member toward the distal end of the at least one syringe until a desired load on the at least one drive member is reached; measure and store a contact position of the at least one drive member within the at least one syringe, wherein the contact position is a position where the desired load is reached; and derive a slack correction volume based at least partially on the difference between the reference position and the contact position.

Clause 16. The system of clause 15, wherein the processor of the fluid injector is programmed or configured to switch the at least one valve between the first position, the second position, and the third position.

Clause 17. The system of clause 15 or 16, wherein the processor of the fluid injector is programmed or configured to relieve pressure in the at least one syringe.

Clause 18. A method for characterizing and correcting fluid injection system slack, the method comprising: driving at least one drive member of a fluid injector to a distal end of at least one syringe connected to the fluid injector; retracting the at least one drive member toward a proximal end of the at least one syringe to draw fluid into the at least one syringe from at least one fluid container in fluid communication with the at least one syringe; switching at least one valve from a first position where the at least one syringe is in fluid communication with the at least one fluid container to a second position where the at least one syringe is isolated from the at least one fluid container to isolate the at least one syringe from the at least one part of the fluid injection system; measuring and storing a reference position of the at least one drive member within the at least one syringe; driving the at least one drive member toward the distal end of the at least one syringe until a desired load on the at least one drive member is reached; measuring and storing a contact position of the at least one drive member within the at least one syringe, wherein the contact position is a position where the desired load is reached; and deriving a slack correction volume based at least partially on the difference between the reference position and the contact position.

Clause 19. The method of clause 18, further comprising evacuating the fluid from the at least one syringe; filling the at least one syringe with a desired volume of fluid plus an additional volume of fluid equal to the slack correction volume; and delivering the fluid from the at least one syringe to a patient.

Clause 20. The method of clause 18 or 19, wherein the method steps are performed at least partially by a processor configured to control a motor driving the at least one drive member of the injector.

Clause 21. The method of any of clauses 18 to 20, wherein the slack correction volume is determined at an initial use of the at least one syringe.

Clause 22. The method of any of clauses 18 to 21, further comprising repeatedly measuring and storing the slack correction volume over time to develop a slack curve of the at least one drive member of the at least one injector as a function of time.

Clause 23. The method of any of clauses 18 to 22, further comprising alerting a user if a measured slack correction volume for the at least one drive member is significantly different from an expected slack correction volume based on the slack curve for the at least one drive member.

Clause 24. A method for characterizing and correcting fluid injection system slack, the method comprising: driving at least one drive member of a fluid injector to a distal end of at least one syringe connected to the fluid injector; retracting the at least one drive member toward a proximal end of the at least one syringe to draw fluid into the at least one syringe from at least one fluid container in fluid communication with the at least one syringe; switching at least one valve from a first position where the at least one syringe is in fluid communication with the at least one fluid container to a second position where the at least one syringe is isolated from the at least one fluid container to isolate the at least one syringe from the at least one part of the fluid injection system; driving the at least one drive member toward the distal end of the at least one syringe until a desired load on the at least one drive member is reached; measuring and storing a contact position of the at least one drive member within the at least one syringe; relieving pressure from the at least one syringe until a pressure within the at least one syringe is equal to where the at least one drive member has no applied load; measuring and storing a reference position of the at least one drive member within the at least one syringe where the pressure within the at least one syringe is equal to the pressure applied by the at least one drive member; and deriving a slack correction volume based at least partially on the difference between the reference position and the contact position.

Clause 25. The method of clause 24, further comprising evacuating the fluid from the at least one syringe; filling the at least one syringe with a desired volume of fluid plus an additional volume of fluid equal to the slack correction volume; and delivering the fluid from the at least one syringe to a patient.

Clause 26. The method of clause 24 or 25, wherein the method steps are performed at least partially by a processor configured to control a motor driving the drive member of the injector.

Clause 27. The method of any of clauses 24 to 26, wherein the slack correction volume is determined at an initial use, for example an initial fill, of the at least one syringe.

Clause 28. The method of any of clauses 24 to 27, further comprising repeatedly measuring and storing the slack correction volume over time to develop a slack curve of the at least one drive member of the at least one injector as a function of time.

Clause 29. The method of any of clauses 24 to 28, further comprising alerting a user if a measured slack correction volume for the at least one drive member is significantly different from an expected slack correction volume based on the slack curve for the at least one drive member.

These and other features and characteristics of a system for position calibration of a drive mechanism of a fluid injector, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only.

DETAILED DESCRIPTION

Figure 1:
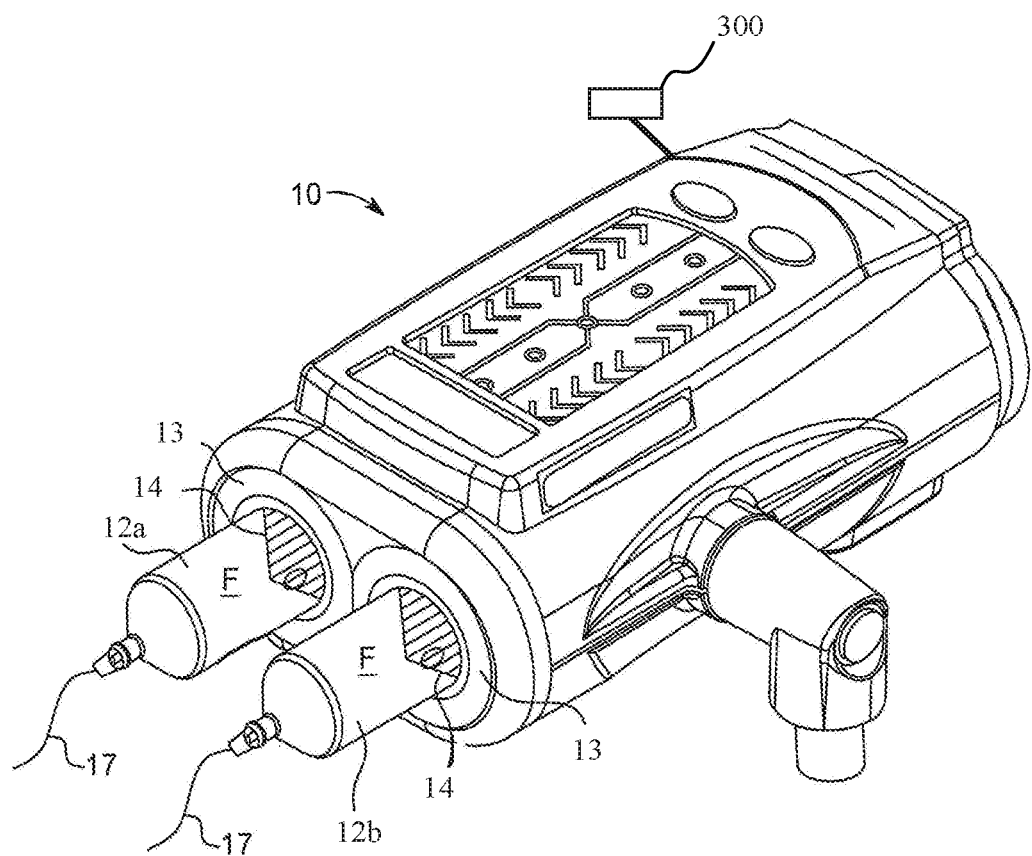
FIG. 1 is a perspective view of a fluid delivery system according to an example of the present disclosure.

As used in the specification and the claims, the singular form of "a", "an", and "the" include plural referents unless the context clearly dictates otherwise.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures.

Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". The term "about" means a range of plus or minus ten percent of the stated value.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

The term "at least" means "greater than or equal to".

The term "includes" is synonymous with "comprises".

When used in relation to a syringe and/or a plunger, the term "proximal" refers to a portion of a syringe and/or a plunger nearest a fluid injector when a syringe and/or a plunger is oriented for connecting to a fluid injector. The term "distal" refers to a portion of a syringe and/or a plunger farthest away from a fluid injector when a syringe and/or a plunger is oriented for connecting to a fluid injector. The term "radial" refers to a direction in a cross-sectional plane normal to a longitudinal axis of a syringe, a plunger, and/or a piston extending between proximal and distal ends. The term "circumferential" refers to a direction around an inner or outer surface of a sidewall of a syringe, a plunger, and/or a piston. The term "axial" refers to a direction along a longitudinal axis of a syringe, a piston, and/or a piston extending between the proximal and distal ends. The term "open" when used to refer to a fluid delivery component means that the system is in fluid connection with an outlet, for example through a nozzle or the open end of a tubing component or catheter. In an open system, fluid flow may be constrained, for example by forcing a fluid through a small diameter fluid path where flow may be determined by physical parameters of the system and the fluid, such as tubing diameter, fluid path constrictions, applied pressure, viscosity, etc. The term "closed" when used to refer to a fluid delivery component means that the system is not in fluid connection with an outlet, for example where fluid flow is stopped by a valve, such as a stopcock, high crack pressure valve, pinch valve, and the like. As used herein the term "slack" means mechanical slack, including a clearance or lost motion in a mechanism caused by gaps between parts, compression of mechanical components under applied load (such as by applied pressure), deflection of mechanical components under applied load (such as by applied pressure), that results in a delay of pressurized delivery of a fluid from a fluid injection after application of force.

It is to be understood that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the examples disclosed herein are not to be considered as limiting.

Characterizing an impedance of a fluid delivery system to minimize a difference between desired and actual fluid delivery system performance requires consideration of how energy from an energy source is used in or moves through the system. The energy output or loss from the fluid delivery system may be in the form of heat losses through frictional forces or of work done on the fluid delivery system. For example, some of the energy carried by the pressurized fluid as it is delivered under pressure through a catheter is lost through resistive, frictional, or dissipative heating of the fluid. Additionally, pressurized delivery of fluid can also increase the potential energy of the system in terms of an increase in overall volume of system components or compressive forces on system components, as discussed herein. Furthermore, the kinetic energy of pressurized fluid moving through the fluid delivery system can affect the overall performance of the fluid delivery system. For example, inertial forces of moving contrast material and expansion of the containers and/or tubing associated with the system may cause a phase lag between movement of the syringe plunger within the injector syringe and movement of contrast material out of the catheter and into the patient.

Due to high injection pressures, which may be on the order of 1,200 psi in some angiographic procedures, there may be an expansion, deflection, or compression of various components of the fluid delivery system, such as the syringes, tubing connected to the patient, and components of the fluid injector, such that there may be a volume of fluid in the syringe and tubing in excess of the desired quantity selected to be delivered in the injection procedure. Such increase in the quantity of fluid occurs due to system capacitance. Total system capacitance (also referred to as compliance or elasticity) represents the amount of fluid (i.e., change in volume, such as excess volume) that is captured in the swelling of the components of the fluid delivery system. In general, capacitance is directly correlative to injection pressure and inversely correlative to volume of contrast medium and saline in the syringes. In other words, capacitance increases with an increase in injection pressure and an increase in volume of fluid in the syringes. Total system capacitance is inherent to each fluid delivery system and depends on a plurality of factors beyond pressure and volume of fluid remaining in the system, including, without limitation, injector construction, mechanical properties of materials used to construct the syringe, plunger, pressure jacket surrounding the syringe, and fluid lines delivering the fluid to the patient, size of the syringe, plunger, pressure jacket, diameter of tubing or other orifices through which the fluid must pass under pressure, and fluid properties, such as temperature, viscosity, and density.

Additionally, inefficiencies in the drivetrain of the injection system, such as those due to tolerances in various components of the drive mechanism and/or wear over time, can add further uncertainty to the difference between a desired volume and flow rate of fluid to be delivered, and the volume and flow rate that are actually delivered. These inefficiencies may create slack, and can result in an aggregated difference between the desired volume and/or flow rate of fluid to be delivered, and the actual volume and or flow rate of fluid delivered.

While various approaches exist for characterizing the performance of a fluid delivery system and correlating the desired performance with actual performance in terms of fluid flow rate and volume delivered, these approaches do not address the differences between desired and actual performance due to impedance and/or capacitance of the fluid delivery system in a comprehensive manner. As a result, existing approaches fail to address the under-delivery or over-delivery of fluid resulting from system impedance and/or capacitance. As a result, less than optimal injection boluses or volumes may result and/or operation of the fluid delivery system can result in relatively large amounts and/or large volumes of wasted medical fluid and/or inefficient use of the delivered volume which may result in lower image quality.

In some fluid delivery systems, such as fluid delivery systems having two or more syringes independently driven by a drive member of the fluid injector, the accuracy of fluid delivery is based on the ability of the fluid injector to accurately characterize the pressure in the syringes. This characterization is based, at least in part, on calibrating the drive member using a calibration station or fixtures configured for accurately measuring the pressure imparted on a fluid by the drive member. Traditional pressure calibration of fluid injectors may be performed by pushing fluid at varying rates through a frictionless fixture with a fixed orifice. Pressure of the fluid is then measured using a pressure gauge, where a real pressure signal is either recorded or fed back into the fluid injector to correlate the load signal of the drive member, such as voltage or current measurement, to a real pressure value. Conventional calibration stations are cumbersome, difficult to set up and operate, and have compounded errors, leading to inaccurate pressure characterization of the drive member. For example, errors include friction in the fixture, air in the fluid path, lack of data points on a correlative timescale, and gauge reading inaccuracies. Further, conventional calibration does not provide for real-time adjustment based on factors, such as component wear, differences in syringe tolerance, fluid characteristics, and volumes of syringes used since it is performed infrequently, such as when the injector is serviced. Changes in injector components can add up over time to increase volume inaccuracies, such as by changing a zero point used to calibrate the volume accuracies of fluid delivery.

A related problem common to fluid delivery systems is the inability to characterize and correct for slack at the interface of the plunger of the syringe and the piston of the fluid injector. Slack results from an imperfect connection between the piston and plunger which allows some degree of separation of the plunger relative to the piston during operation of the fluid delivery system. Major contributing factors to slack include the manufacturing tolerances for components of the plunger, the piston, and/or components of a drive motor, which result in components that fit together with varying degrees of imperfection or tolerance. Tolerances may also be designed into the components for ease of use. Another major source of slack includes component wear which causes the fit between the plunger and piston to loosen with repeated use. Slack may also be introduced from other sources, including backlash on gears and/or ball screws driving the fluid injector, the interface between the syringe and the injector, the interface between piston and plunger, and any other surfaces which experience load during fluid injection.

Slack is most evident in the fluid delivery system during the transition from a filling operation to a delivery operation. During the filling operation, the piston of the fluid injector is drawn away from the tip of the syringe, i.e., in the proximal direction, pulling the plunger along with it. However, system slack, for example at the interface of the piston and plunger, may allow the piston to move a small but significant distance without movement of the plunger, creating a gap between the piston and the plunger. Due to friction between the plunger and the syringe barrel, the gap may be maintained throughout the filling operation. At the transition from the filling operation to the delivery operation, the piston changes direction and moves toward the tip of the syringe, i.e., in the distal direction. However, distal movement of the piston may not immediately induce movement of the plunger, and thus does not cause fluid to be injected until the piston travels the length of the gap corresponding to the slack of the system. This travel may produce inaccuracies in volume of fluid delivered by the fluid injector, such as under delivery, during an injection procedure.

To avoid under delivery of fluid from a fluid delivery system, this slack must be characterized, monitored, and corrected for. Existing methods and systems for characterizing and correcting for slack at the interface of a piston and plunger simply increase the piston travel to compensate for fluid delivery system slack. The increase in piston travel is generally a static value programmed into the controller of the fluid injector during the manufacturing process, for example, based on calculations and measurements from an "ideal" injector and values derived therefrom, such that each delivery operation overdrives the piston by the same predetermined distance. This ideal injector slack distance may be derived from aggregating delivery data of many fluid delivery systems including multiple syringes and plungers, as well as statistical analyses of the machining tolerances of the components of the fluid delivery system. Such delivery data can be used to determine the extra volume of fluid necessary to deliver the desired total volume of fluid. The extra volume may then be converted to overdrive of the piston, and programmed into the individual fluid delivery system.

Existing methods and systems, however, provide only approximate correction for slack because they are based on statistical data gathered from multiple components, in particular pistons, motors, and plungers, at the manufacturing stage from an "ideal" injector and does not address individual variances between injectors, components of injectors, syringes, fluid paths and the like, both at the manufacturing stage and after continual use with associated wear. The actual slack in a specific fluid delivery system can only be determined from the characteristics of the actual components for that system including wear of components over time and variances among batches of disposable components (syringes, plungers etc.). Further, the slack values may change over time due to wear and variances among disposable components. Existing systems and methods, which are not optimized for a specific fluid delivery system and components, are thus prone to problems such as under delivery or over delivery of fluid if the approximated "ideal" slack value differs from the actual slack value. Excess fluid delivery can result in over pressurization of fluid path components causing leaking, dislodging of fluid path components, and, in extreme cases, rupture of fluid path components.

In one embodiment according to the present disclosure, the position of the drive member of the fluid injector system may be calibrated. At least one fluid reservoir, optionally comprising a drive member, may be engaged with the injector and an injector pressurization feature may be operably connected to the drive member. Suitable fluid reservoirs include a syringe (such as a disposable or reusable syringe), a peristaltic pump reservoir, a compressible bag, and combinations thereof. In certain embodiments, the fluid injector may include one fluid reservoir, while other embodiments the fluid injector may include a plurality of fluid reservoirs, such as two, three, or even more fluid reservoirs. Drive members may include plungers for syringes, end walls of enclosed rolling diaphragm syringes, peristaltic pump roller, and compressible clam shell-type drive members. Injector pressurization features include pistons, peristaltic pump drive, and the like. Drive members may be driven by a motive force, such as a reciprocally operable via electromechanical drive components such as a ball screw shaft driven by the motor, a voice coil actuator, a rack-and-pinion gear drive, a linear motor, a linear actuator, a rotary motor, and the like. The motor may be an electric motor. In certain embodiments, where the at least one fluid reservoir is at least one syringe, as described herein, the drive member may be driven distally from a proximal position in the syringe body to a specified distal potion in the syringe body, for example until it contacts the distal end of the interior of the syringe. The drive member continues to be driven distally until a load force value on the distal end of the syringe is reached. The load force value may, for example, be as a result of compressive forces, such as mechanical slack, plunger compression, friction, and deflection, among other forces on the system. The force on the drive member slowly may then be decreased until the load force value reaches zero or a predetermined load force value. The position of the drive member may be recorded as the zero volume, for example, the zero volume position (e.g., in milliliters), for that syringe where all fluid has been expelled from the syringe. The zero volume position may be recorded and saved by a processor associated with the injector for each individual syringe, such as by recording the zero volume position by a processor within its memory, and then used during injection protocols utilizing that syringe to more accurately deliver a desired fluid volume and/or flow rate. Measuring the force and associated change in position between the compressed position and the zero position may be used, for example, to identify or determine the position where at least one of the following occur: the piston contacts the plunger, when the fluid is first compressed, when the plunger first contacts the end of the syringe, when a deflection is detected on a restraint such as a syringe/injector engagement restraint, when a valve is cracked such as a high pressure crack valve, when a sidewall of a rolling diaphragm syringe (as described herein) first starts to roll in upon itself, and when the exterior of the syringe contacts a pressure jacket feature. In various embodiments, measuring the force and associated change in position between the compressed position and the zero position may be used to determine a priming volume as part of a start of day or start of new injector protocol process. In other embodiments, the measuring of force and/or change in associated position may be used to detect when a priming or purging operation is completed, for example by detecting a change in pressure force associated with the transition from expelling air to expelling a liquid. In other embodiments, the measuring of force and/or change in associated position may be used to check the fidelity of a valve seal or other component in the fluid injector system. According to various embodiments, the load or strain on a system component may be measured, for example by a pressure sensor, a strain gauge, a measure of motor current or combinations of any thereof. In embodiments, where the drive member is a piston/plunger mechanism for a syringe, the processor may determine and store the strain on a linear motor and/or displacement of the piston and/or plunger. In embodiments where the drive member may be a peristaltic-type pump, the processor may store the amount of partial or full rotations of the roller pump and in embodiments where the reservoir is a compressible bag, the processor may determine and store the distance to compress the bag.

According to embodiments, where the fluid injection system comprises a peristaltic pump or utilizes an angular compressive movement, for example to compress a compressible bag, such as a clam-shell configuration, the methods described herein may also provide calibration of the drive member. For example, in one embodiment, the method may include placing the fluid reservoir or pump in fluid isolation, for example by closing a valve, as described herein. Once the system is fluidly isolated, the drive member, for example a rotor pump or angularly compressive force, may pressurize the fluid in the reservoir to a first predetermined pressure. The displacement of the drive member required to reach the first predetermined pressure is recorded and the drive member is further driven to pressurize the fluid in the closed system to a second predetermined pressure and the additional displacement of the drive member to reach the second predetermined pressure is recorded. The difference between the drive member displacement to reach the first predetermined pressure and the displacement required to reach the second predetermined pressure is calculated and the value is used to calibrate the fluid injection system and position of the drive member to account for mechanical slack and/or system compliance. Once the system is calibrated, the processor may use this calibration to correct for fluid flow inaccuracies during an injection procedure to deliver an accurate fluid volume.

In another embodiment of the present disclosure the drive member may pull a vacuum on the fluid reservoir for determining the zero position for the reservoir and drive member. In various embodiments the position of the drive member of the fluid injector system may be calibrated according to the following process. The drive member may be moved proximally from a distal position in the syringe body thereby drawing a vacuum load within the reservoir, for example a syringe, until it reaches a predetermined vacuum load. The force on the drive member may then be released and the drive member may move distally until the vacuum load force value reaches zero or a predetermined vacuum load force value. The position of the drive member is recorded as the zero volume position for that syringe. The zero volume position may be recorded and saved by the injector for each individual syringe, such as by recording the zero position by a processor within its memory, and then used during injection protocols utilizing that syringe to more accurately deliver a desired fluid volume and/or flow rate.

In embodiments according to the present disclosure injector may be in communication with a processor, for example a processor associated with the injector, a separate processing unit, a hospital information network processor, or a processor connected by a wired or wireless method. The various embodiments of the method may be stored in memory, controlled by a processor and/or an operator, and carried out automatically or manually whenever a new syringe or set of syringes is connected to the injector or at the start of a new injection protocol. According to other examples, this method may be carried out at the prompting of a user or the processor may prompt a user and recommend that the method be carried out.

In other embodiments, a method of the present disclosure may be used to track wear on injector mechanical components, such as the motor or drive train, or on a fluid reservoir or fluid path, for example a syringe and/or tube set, over multiple uses or injection protocols. According to these embodiments, changes in the zero volume position may be tracked over a period of time, such as over a specified period of use for the injector or the use-life of the fluid reservoir/syringe and or tube set to monitor component wear or failure. In other examples, the methods of the present disclosure may be used to track wear on the injector components and/or a batch of syringes if applied to the batch of syringes over time, wherein the zero volume positions of the syringes are tracked and changes in the zero volume position is monitored over time. This may have applications in predictive maintenance of the injector, and the syringes. If excessive or sudden wear or failure is detected, the component may be repaired or replaced to avoid additional damage to the injector or injury to the patient or operator.

In other embodiments, a method according to the present disclosure may be used to verify whether a fluid reservoir, such as a syringe or fluid path, is faulty, for example if the zero volume position is outside of a pre-determined range, wherein the determined range is representative of normal variance within the accepted syringe tolerances. In examples, a zero volume position that is too proximal along the longitudinal axis, relative to the predetermined range, may indicate a fault condition, such as a cocked or misaligned plunger. A zero volume position that is too far distal along the longitudinal axis, relative to the predetermined range, may indicate other problems or fault conditions such as a leak or weakness in a valve, fluid path, or fluid reservoir. Either boundary issue relative to the expected predetermined range may indicate an error or alarm condition to the user with respective notification to the user via a visual and/or audible alert, and in certain conditions may cause the injector to cease injection procedures until the error is corrected.

In other embodiments, the method according to the present disclosure may be used to measure recoil of a plunger or a syringe as an indication of wear of injector components or wear of syringe components in a multi-use syringe set.

In other embodiments, the method according to the present disclosure may measure static or dynamic friction of the plunger and/or the interior surface of the syringe body at the beginning of injection procedures, and initial values may be compared to expected, standard values, or measured values over time for a syringe design. Static and/or dynamic friction may be compared to known coefficients of friction of silicone, silicone compounds, and/or mixtures containing silicone to assess the presence or absence of silicone in the plunger and/or syringe. This may provide information on production standards for various production batches of syringes.

In some examples of the present disclosure, a fluid injector system for delivering fluid to a patient includes a fluid injector having a processor and at least one piston, and at least one syringe removably connected to the fluid injector and including a plunger disposed in a barrel of the at least one syringe and reversibly movable along a longitudinal axis of the syringe. In certain embodiments, the fluid injector may include two or more syringes, three syringes, or even greater than three syringes for injecting saline and one or more contrast media or other medical fluids. The at least one piston of the fluid injector may be configured to engage the plunger of the at least one syringe and travel along the longitudinal axis inside the barrel of the at least one syringe, and at least one valve is in fluid communication with the at least one syringe and at least one fluid container. The valve may be switchable between a first position in which the at least one syringe is in fluid communication with the at least one fluid container and isolated from fluid communication with a patient (i.e., a first open position), a second position in which the at least one syringe is isolated from fluid communication with both the at least one fluid container and the patient (i.e., a closed position), and a third position where the at least one syringe is isolated from fluid communication with the fluid container and in fluid communication with a patient (i.e., a second open position). The processor may be associated with the fluid injector and may be programmed or configured to provide one or more commands including commands to drive the at least one piston of the fluid injector to a distal end of the at least one syringe, retract the at least one piston toward a proximal end of the at least one syringe to draw fluid into the at least one syringe from the at least one fluid container, measure and store a reference position of the at least one piston within the at least one syringe, switch the at least one valve from the first position to the second position, drive the at least one piston toward the distal end of the at least one syringe until a desired load on the piston is reached, measure and store a contact position of the at least one piston within the at least one syringe, wherein the contact position is a position where the desired load is reached, and derive a slack correction volume based at least partially on the difference between the reference position and the contact position. The processor may then calibrate the injector and/or syringe based on the stored correction volume. In other examples of the present disclosure, the processor of the fluid injector may be programmed or configured to switch the at least one valve between the first open position and the second closed position. By controlling the valve position, the injector may calculate and calibrate the system in the open state or the closed state.

In other examples of the present disclosure, the processor of the fluid injector may be programmed or configured to relieve pressure in the at least one syringe after a pressurizing stroke by the drive member when the syringe is part of a closed system, for example by either moving the drive member and plunger in a proximal direction, for example by small incremental releases of the load force or by releasing the load force at a predetermined rate until the load force value is reduced to zero, which may indicate a zero position (i.e., no further proximal movement of the plunger) is observed, or alternatively by releasing all load force applied to the plunger and allowing the drive member to move freely in the proximal direction as the pressure within the syringe is equalized. According to embodiments, measurement of when the proximal movement of the plunger ceases may provide a zero position that may be used to calibrate the injector components associated with the syringe. In other embodiments, the system may repeatedly determine and store a slack correction volume over a specified time period, for example, at an initial use of the at least one syringe or at the beginning of the day, week, month, or other selected time period. Once repeated measurements have been taken and stored for the slack correction volume over time, the fluid injector, for example the processor, may develop a slack curve for each piston of the injector as a function of time. The injector may then be configured to provide an alert to a user if a measured slack correction volume for at least one piston is significantly different from an expected slack correction volume based on the slack curve for the at least one piston.

Referring to the drawings in which like reference characters refer to like parts throughout the several views thereof, the present disclosure is generally directed to fluid injector and a system and method for calibration of the fluid injector. Associated disclosure related to capacitance development and issues associated with fluid injection system is described in PCT International Application No. PCT/US2017/020637, filed 3 Mar. 2017, the disclosure of which is incorporated herein by this reference.

With reference to FIG. 1, a fluid injector 10 (hereinafter referred to as "injector 10"), such as an automated or powered fluid injector, is adapted to interface with and actuate one or more syringes 12 (hereinafter referred to as "syringe 12"), which may be filed with a fluid F, such as contrast media, saline solution, or any desired medical fluid. The injector 10 may be used during a medical procedure to inject the medical fluid into the body of a patient by driving a plunger 14 of each syringe 12 with a drive member, such as piston 19 (shown in FIG. 2), such as linear actuator or a piston element. The injector 10 may be a multi-syringe injector having two, three or more syringes, wherein the several syringes 12 may be oriented in a side-by-side or other relationship and may be separately actuated by respective drive members/pistons 16 associated with the injector 10. In examples with two or more syringes, for example, arranged in a side-by-side or other relationship and filled with two different fluids, the injector 10 may be configured to deliver fluid from one or both of the syringes 12, sequentially or concurrently. The fluid injector 10 may have at least one bulk fluid source (not shown) for filling the syringes 12 with fluid. In examples, the injector 10 may be operably connected to a computing device 300 having a controller and memory.

A fluid path set 17 may be in fluid communication with each syringe 12 to place each syringe in fluid communication with a catheter for delivering the fluid F from each syringes 12 to a catheter (not shown) inserted into a patient at a vascular access site. In certain embodiments, fluid flow from the one or more syringes 12 may be regulated by a fluid control module (not shown) that operates various valves, stopcocks, and flow regulating structures to regulate the delivery of the saline solution and contrast to the patient based on user selected injection parameters, such as injection flow rate, duration, total injection volume, and ratio of fluids from the syringes 12, including specific ratios of each fluid in a dual flow injection protocol.

Figure 2:
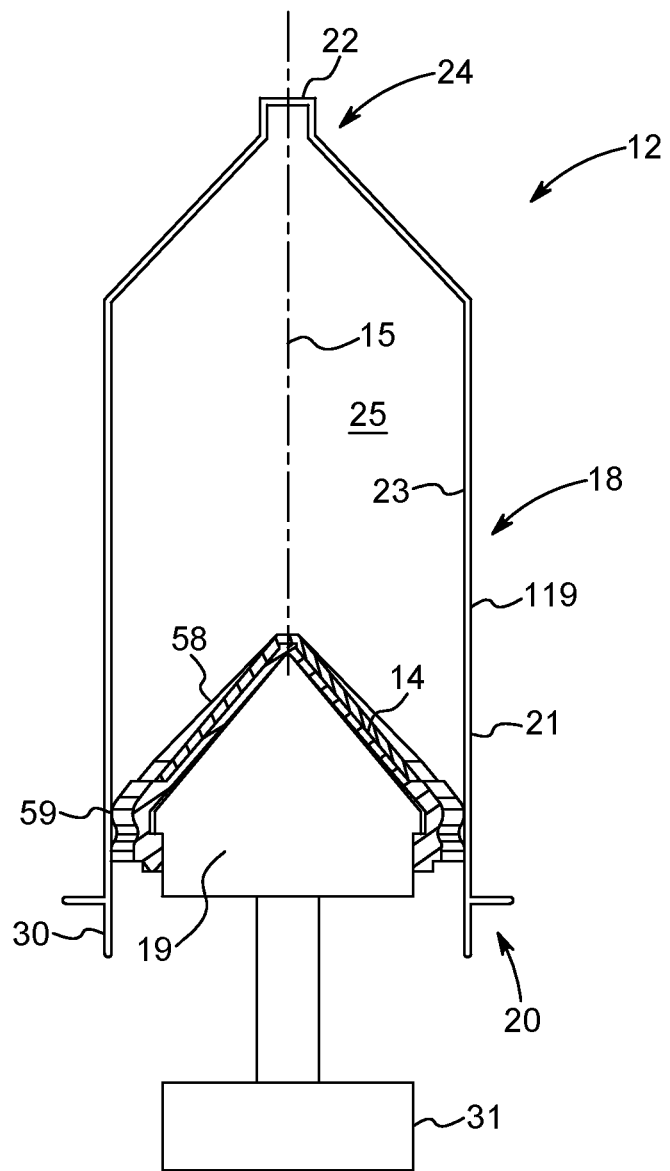
FIG. 2 is a side cross-sectional view of a syringe configured for use with the fluid delivery system of FIG. 1.

With continued reference to FIG. 2, the drive member 19, such as a reciprocally driven piston moved by a motor 31, may be configured to extend into and from the respective syringe port 13 through an opening in the front end of the injector housing. In fluid injector embodiments comprising a plurality of syringes, a separate drive member/piston 19 may be provided for each syringe 12. Each drive member/piston 19 is configured to impart a motive force to at least a portion of the syringe 12, such as the plunger 14 or a distal end of a rolling diaphragm syringe (for example, as described in PCT/US2017/056747; WO 2016/172467; and WO 2015/164783, the disclosures of which are incorporated herein by this reference). The drive member or piston 19 may be reciprocally operable via electro-mechanical drive components such as a ball screw shaft driven by the motor 31, a voice coil actuator, a rack-and-pinion gear drive, a linear motor, a linear actuator, and the like. The motor 31 may be an electric motor.

Examples of suitable front-loading fluid injectors 10 are disclosed in U.S. Pat. Nos. 5,383,858; 7,553,294; 7,666,169; 9,173,995; 9,199,033; and 9,474,857; and in PCT Application Publication Nos. WO 2016/191485 and WO 2016/112163, the disclosures of which are incorporated by reference in their entirety.

Having described the general structure and function of specific embodiments of the fluid injector 10, an embodiment of syringe 12 configured for use with the injector 10 will now be described with reference to FIG. 2. The syringe 12 generally has a cylindrical syringe barrel 18 formed from glass, metal, or a suitable medical-grade plastic. The barrel 18 has a proximal end 20 and a distal end 24, with a sidewall 119 extending therebetween along a length of a longitudinal axis 15 extending through a center of the barrel 18. In some examples, the distal end 24 may have a conical shape that narrows in a distal direction from the cylindrical barrel 18. A nozzle 22 extends from the distal end 24. The barrel 18 has an outer surface 21 and an inner surface 23 with an interior volume 25 configured for receiving the fluid therein. The proximal end 20 of the barrel 18 may be sealed with the plunger 14 that is reciprocally movable through the barrel 18 by reciprocal movement of the corresponding piston 19 or drive member. The plunger 14 forms a liquid-tight seal against the inner surface 23 of the barrel 18 as the plunger 14 is advanced moved through the barrel 18. The injector 10 may be associated with and operatively connected to a processor 300, such as a computing device having a controller and memory, for example by a wired or wireless (wifi, Bluetooth etc.) connection such that operation of the injector and various data points determined therefrom may be stored and utilized in calculations and injector protocols.

With continued reference to FIG. 2, the proximal end 20 of the syringe 12 is sized and adapted for being removably inserted in a syringe port 13 of an injector 10 (shown in FIG. 1). In some examples, the proximal end 20 of the syringe 12 defines an insertion section 30 that is configured to be removably inserted into the syringe port 13 of the injector 10 while the remaining portion of the syringe 12 remains outside of the syringe port 13.

The syringe 12 may be made of any suitable medical-grade plastic or polymeric material, desirably a clear or substantially translucent plastic material. The material of the syringe 12 is desirably selected to meet the required tensile and planar stress requirements, water vapor transmission, and chemical/biological compatibility. Exemplary syringes suitable for use with the injector 10 depicted in FIG. 1 are described in U.S. Pat. Nos. 5,383,858; 6,322,535; 6,652,489; 9,173,995; and 9,199,033, the disclosures of which are all incorporated by reference in their entirety.

Figure 3:
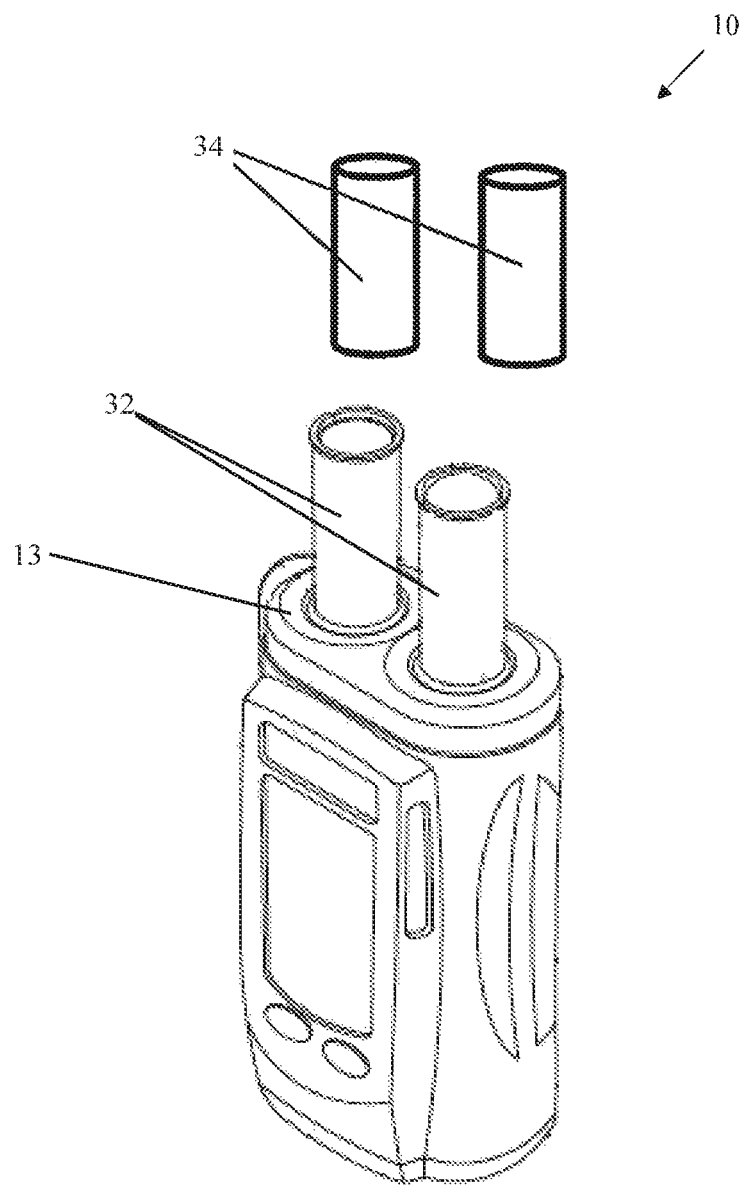
FIG. 3 is a perspective view of a fluid delivery system according to another example of the present disclosure.

In some examples, such as shown in FIG. 3, the injector 10 may be configured for receiving and retaining a pressure jacket 32 within each syringe port 13 of the injector 10. While FIGS. 1 and 3 illustrate fluid injectors 10 with two syringe ports 13, which for the injector 10 shown in FIG. 3 each having a corresponding pressure jacket 32, other examples of the fluid injector 10 may include a single syringe port 13 and optionally, a corresponding pressure jacket 32 or more than two syringe ports 13 with an optional corresponding number of pressure jackets 32. In embodiments comprising pressure jackets, each pressure jacket 32 may be configured to receive a syringe, such as a syringe for an angiographic (CV) procedure, or a rolling diaphragm syringe 34 (suitable examples of which are described in described in PCT/US2017/056747; WO 2016/172467; and WO 2015/164783). A fluid path set, similar to the fluid path set 17 shown in FIG. 1, may be fluidly connected with a discharge end of each rolling diaphragm syringe 34 for delivering fluid from the syringes 34 through tubing connected to a catheter, needle, or other fluid delivery connection (not shown) inserted into a patient at a vascular access site. According to various embodiments, the syringe 12 or 34 may be a pre-filled syringe, i.e., the syringe may be prefilled with a medical fluid, such as a contrast agent or saline, when provided by the syringe manufacturer. According to certain embodiments, the pre-filled syringe may be required to be spiked or otherwise punctured at the discharge end prior to an injection procedure to allow fluid to be expelled from the syringe into a fluid line to the patient, as described herein. The fluid injector 10 may have at least one bulk fluid source (not shown) for filling the syringes 12 with fluid. In examples, the injector 10 may be operably connected to a computing device 300 having a controller and memory.

Figure 4:
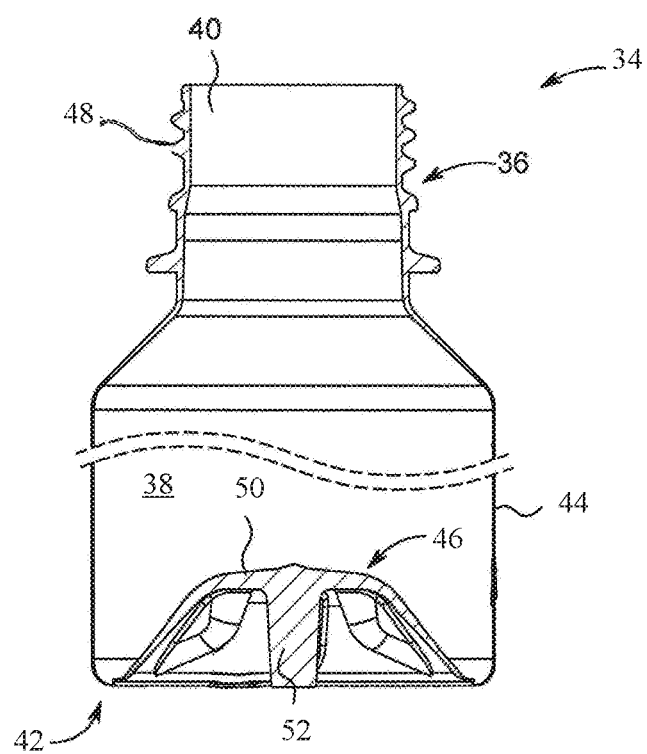
FIG. 4 is a side cross-sectional view of a syringe configured for use with the fluid delivery system of FIG. 3.

With reference to FIG. 4, the rolling diaphragm syringe 34 generally includes a hollow body 36 defining an interior volume 38. The body 36 has a forward or distal end 40, a rearward or proximal end 42, and a flexible sidewall 44 extending therebetween. The proximal end 42 may be configured to act as piston to pressurize the syringe interior to draw in or expel fluid therefrom, as described herein. The sidewall 44 of the rolling diaphragm syringe 34 defines a soft, pliable or flexible, yet self-supporting body that is configured to roll upon itself, as a "rolling diaphragm", under the action of the a drive member or piston of the fluid injector 10. The drive member/piston 19 may be configured to releasably engage a drive member engagement portion 52 at the proximal end 42 of the rolling diaphragm syringe 34 (examples of which are described in PCT/US2017/056747). In operation, the sidewall 44 is configured to roll such that its outer surface is folded and inverted in a radially inward direction as the drive member/piston 19 moves the proximal end 42 in a distal direction and unrolled and unfolded in the opposite manner in a radially outward direction as the drive member/piston 19 retract the proximal end 42 in a proximal direction.

With continued reference to FIG. 4, the rearward or proximal portion of the sidewall 44 connects to a closed end wall 46, and a forward or distal portion of the sidewall 44 defines a discharge neck 48 opposite the closed end wall 46. The closed end wall 46 may have a concave shape to facilitate the initiation of the inversion or rolling of the sidewall 44, enhance mechanical strength of the closed end wall 46, and/or to provide a receiving pocket to receive a distal end of drive member/piston 19. For example, the closed end wall 46 may define a receiving end pocket for interfacing directly with a similarly-shaped distal end of the drive member/piston 19. In some examples, at least a portion of the drive member/piston 19 may be shaped to substantially match the shape of the closed end wall 46 or, alternatively, pressure from the drive member/piston 19 as it is moved distally may conform the end wall 46 to substantially match the shape of at least a portion of the drive member/piston 19.

The end wall 46 may have a central portion 50 having a substantially dome-shaped structure and a drive member engagement portion 52 extending proximally from the central portion 50. The drive member engagement portion 52 is configured for releasably interacting with a corresponding engagement mechanism on the drive member/piston 19 of the fluid injector 10, for example as the drive member/piston is retracted. The rolling diaphragm syringe 34 may be made of any suitable medical-grade plastic or polymeric material, desirably a clear or substantially translucent plastic material. The material of the rolling diaphragm syringe 34 is desirably selected to meet the required tensile and planar stress requirements, water vapor transmission, and chemical/biological compatibility.

Figure 5:
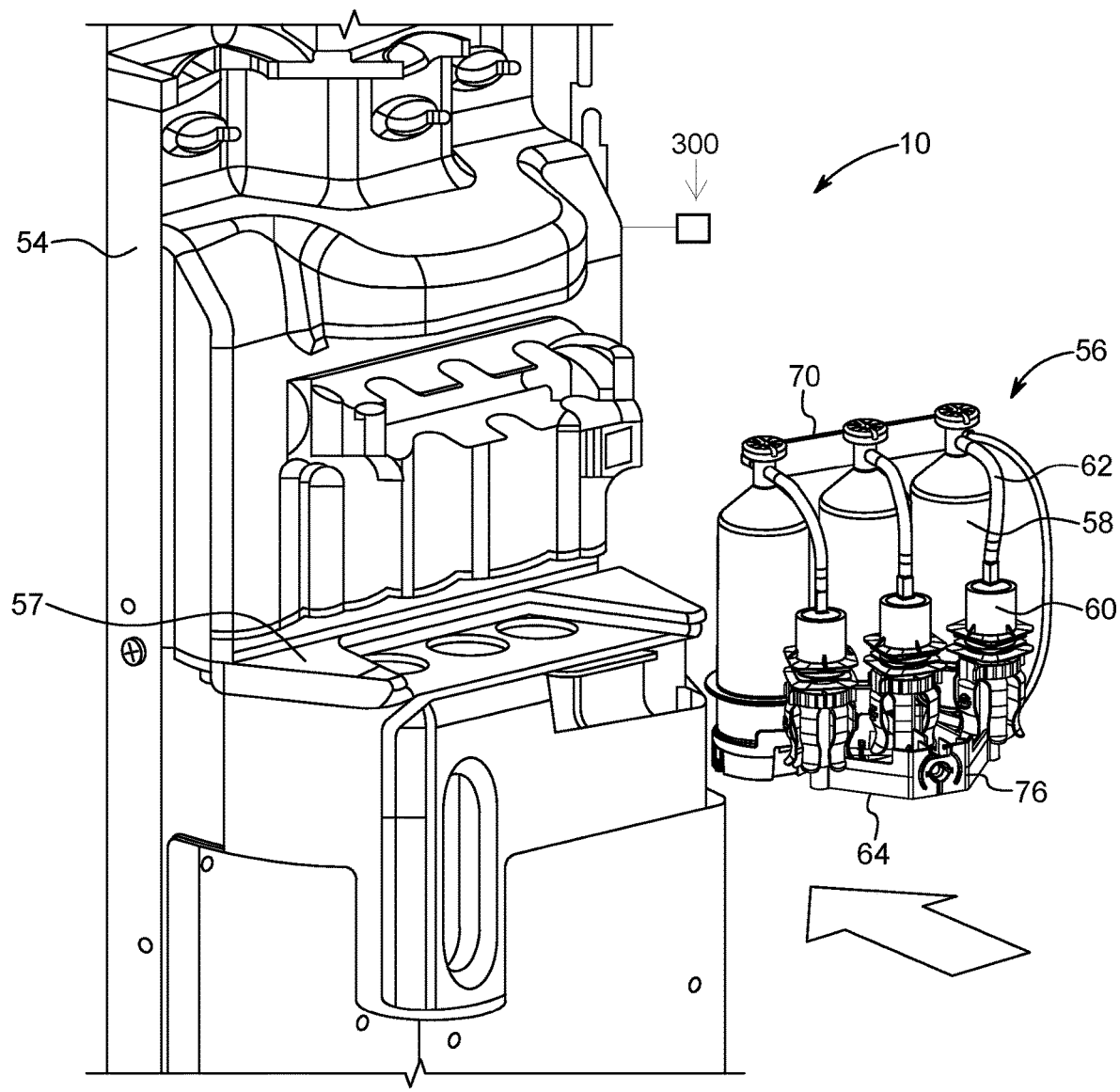
FIG. 5 is a perspective view of a fluid delivery system according to another example of the present disclosure.
Figure 6:
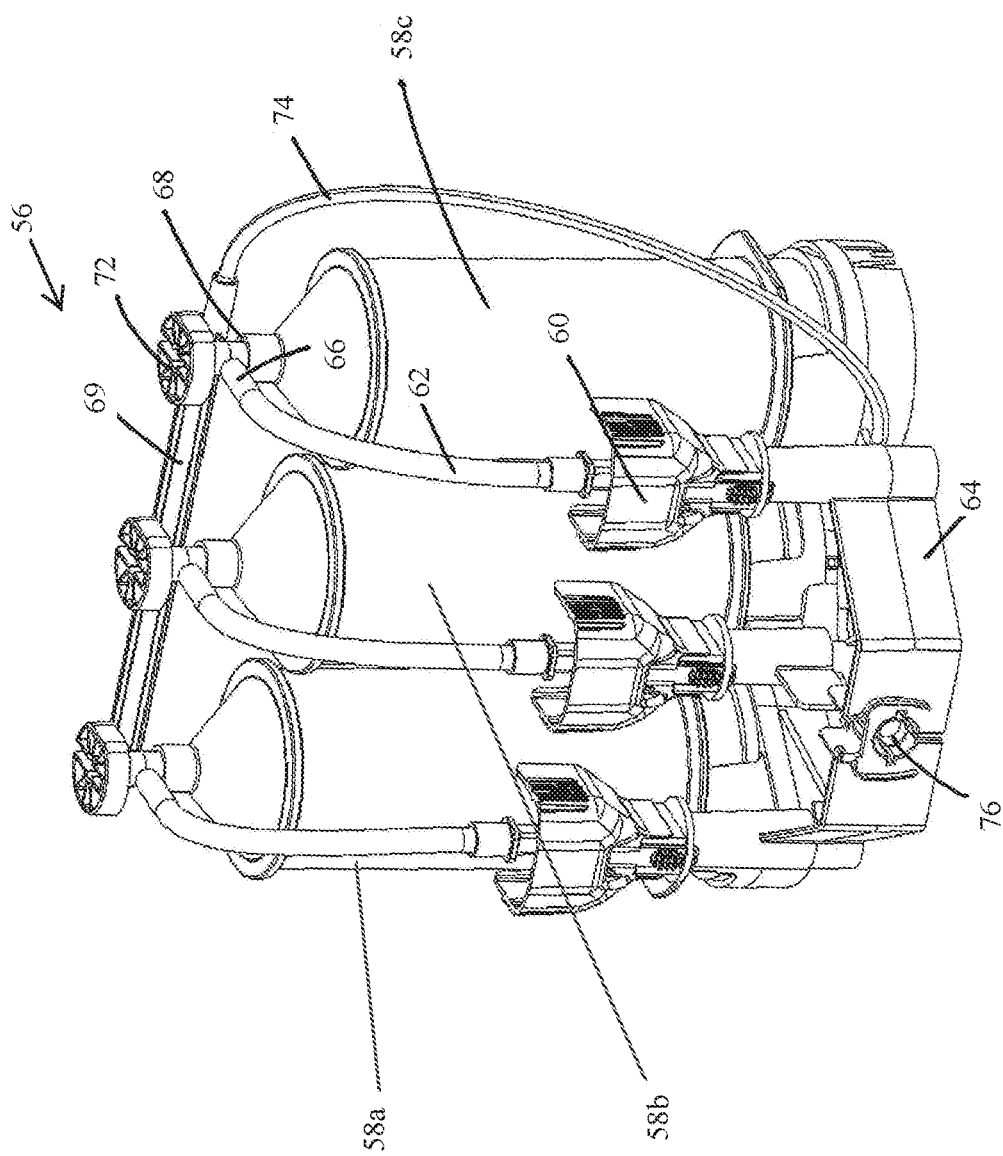
FIG. 6 is a front perspective view of a multi-use disposable system configured for use with the fluid delivery system of FIG. 5.

With reference to FIG. 5, a fluid injector 10 is shown in accordance with another example of the present disclosure. The injector 10 has a housing 54 that encloses various mechanical drive components, electrical and power components necessary to drive the mechanical drive components, and control components, such as electronic memory and electronic control devices used to control operation of reciprocally movable pistons (not shown). The fluid injector 10 further has a multi-patient disposable system (MUDS) 56 that is removably connectable with the fluid injector 10. The MUDS 56 has one or more syringes or pumps 58. In some aspects, the number of syringes 58 corresponds to the number of pistons on the fluid injector 10. In some examples, such as shown in FIG. 6, the MUDS 56 has three syringes 58 in a side-by-side arrangement. Each syringe 58 has a bulk fluid connector 60 for connecting to a respective bulk fluid source (not shown) via a MUDS fluid path 62. The MUDS fluid path 62 may be formed as a flexible tube with a spike element at its terminal end that connects to the bulk fluid connector 60. The fluid injector 10 may have at least one bulk fluid source (not shown) for filling the syringes 12 with fluid. In examples, the injector 10 may be operably connected to a computing device 300 having a controller and memory. Injector 10 and the corresponding MUDS 56 as illustrated in FIG. 5 are described in detail in WO 2016/112163, the disclosure of which is incorporated herein by this reference.

With reference to FIG. 6, the MUDS 56 has a frame 64 for supporting the one or more syringes 58. The syringes 58 may be removably or non-removably connected to the frame 64. Each syringe 58 has an elongated, substantially cylindrical syringe body. Each syringe 58 has a filling port 66 in fluid communication with the MUDS fluid path 62 for filling the syringe 58 with fluid from a bulk fluid source. Each syringe 58 further has a discharge outlet or conduit 68 at the terminal portion of its distal end. The discharge outlet 68 of each syringe 58 is in fluid communication with a manifold 69. A valve 72 is associated with each discharge outlet 68 and is operable between a filling position, where the filling port 66 is in fluid communication with the syringe interior while the discharge outlet 68 is in fluid isolation from the syringe interior, and a delivery position, where the discharge outlet 68 is in fluid communication with the syringe interior while the filling port 66 is in fluid isolation from the syringe interior. The manifold 69 has a fluid pathway that is in fluid communication with each syringe 58 and with a fluid outlet line 74 in fluid communication with a port 76 configured for connecting to a single use fluid path element (not shown) for delivering fluid to the patient. Examples of suitable MUDSs are disclosed in PCT Application Publication No. WO 2016/112163, the disclosure of which is incorporated herein by reference in its entirety.

In various embodiments, for fluid injector 10, for example any of the fluid injectors shown in FIGS. 1, 3, and 5, the motor 31 (FIG. 2) provides the motive force to reciprocally drive the drive member/piston 19 in a distal direction and discharges fluid within the syringes 12, 34 or MUDS 56. The motor 31 may have drive components, such as gears and shafts, that are operatively connected to the drive member/piston 19 to reciprocally move the drive member/piston 19. Each motor 31 must be calibrated to correlate its operating characteristics, such as input current or output torque, to a flow rate or pressure and tolerances associated therewith. As described herein, calibration may be desirable to compensate for any variations or out of specification behavior from any of the different components of the fluid injectors 10, such as any variations in motor performance characteristics, particularly in fluid injectors with two or more syringes driven by two or more motors. For example, conversion of motor input torque for one motor 31 to an injector output pressure may be different for another motor 31. This variation may be further compounded by variations in tolerances of the drivetrain of the fluid injector 10. The accuracy of flow rate or pressure in a fluid injector 10 is directly correlative to a system and method used to calibrate the motor 31. The fluid injector 10 may have at least one bulk fluid source (not shown) for filling the syringes 12 with fluid. In examples, the injector 10 may be operably connected to a computing device 300 having a controller and memory.

Figure 7A:
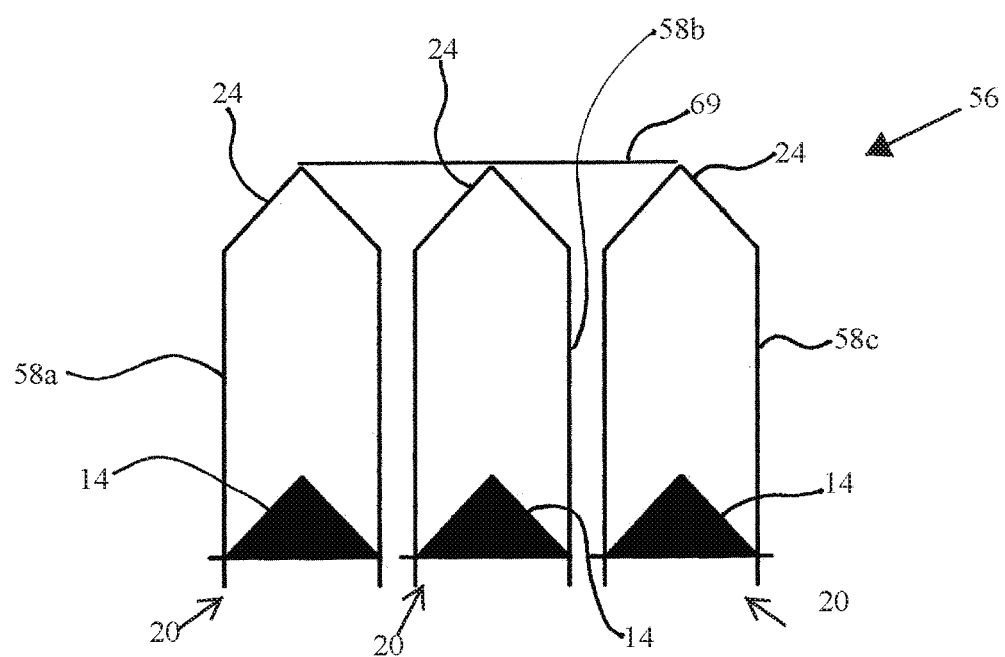
FIG. 7A is a schematic depiction of a multi-use disposable system wherein the plungers of the syringes are disposed in a proximal position.

With reference to FIG. 7A, an example according to the present disclosure may include at least one syringe, such as a previously described MUDS. Each empty syringe 58 is engaged in the injector 54 and plungers 14 are operatively connected to a corresponding piston 19.

Figure 7B:
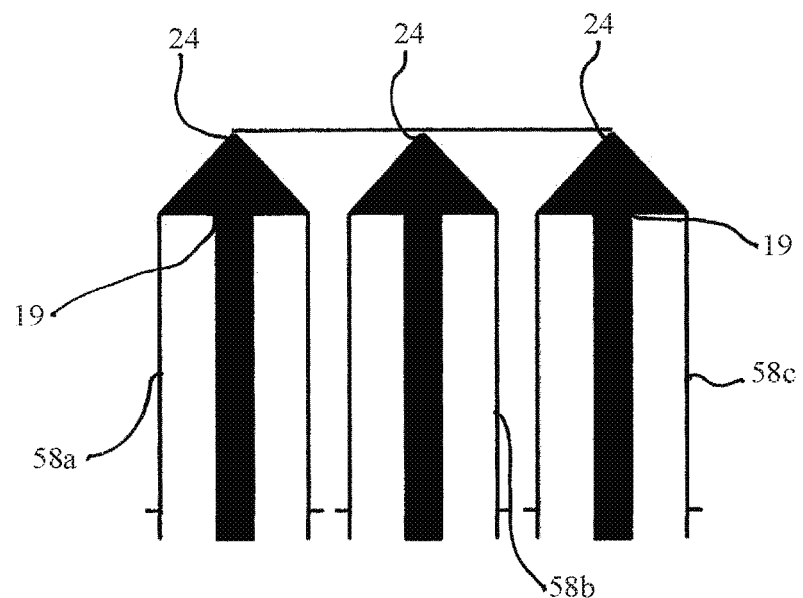
FIG. 7B is a schematic depiction according to FIG. 7A wherein the plungers are driven toward a distal position.

With reference to FIG. 7B, the piston 19, such as one or more linear actuators or reciprocally driven pistons moved by a motor 31 as in FIG. 2, drive the plungers 14 distally along the longitudinal axis 15 of the bodies of the syringes 58, until the plungers contact the distal ends 24 of the syringes 58.

Figure 7C:
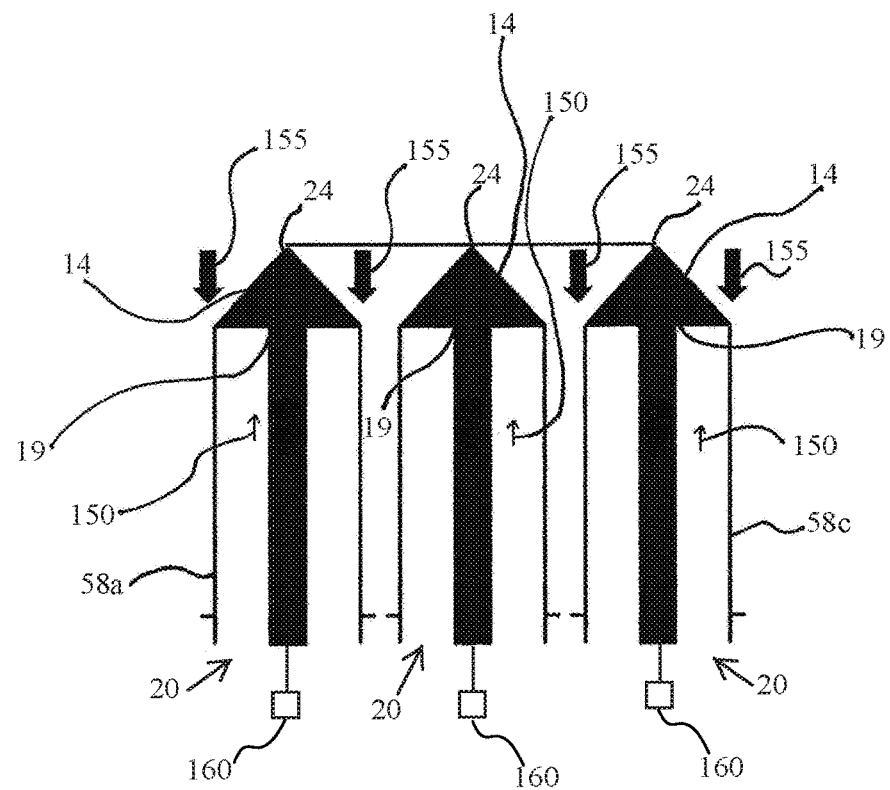
FIG. 7C is a schematic depiction according to FIG. 7A wherein the plungers are disposed and compressed at the distal-most position in the syringes.

With reference to FIG. 7C, even though the distal position of the plungers 14 has been stopped due to their physical contact with the distal ends 24 of the syringes 58 the piston 19 continues to exert force on the corresponding plunger 14 in a distal direction. The direction of the force exerted by the piston 19 is shown by arrows 150. This distal force may compress the plungers 14. The portions of the distal end 24 of the syringe 58 exert a reciprocal force, or load force, on the plunger 14 and the piston 19 in this state in the direction of arrow 155. In an example, this load may be measured for each syringe/piston combination by sensors 160 in operable connection with the plungers 14 and/or the pistons 19. In FIG. 7C, examples of sensors 160 are depicted schematically. Sensors 160 may be pressure sensors, voltage sensors, transducers, or any sensor consistent with the present disclosure known in the art. In an embodiment, the plungers 14 may comprise a material that compresses under the load force.

With further reference to FIG. 7C, the force may be applied by the plungers 14 and/or pistons 19 depicted by arrows 150 until the reciprocal load force depicted by arrows 155 reaches a predetermined level or range. In an example, the load depicted by arrows 155 may range from 25 to 200 psi or in other embodiments range from 50 to 100 psi.

In other examples according to the present disclosure, the force applied may be a load anywhere between zero and the maximum load capable by the motor or piston used by the injector system. In examples according to the present disclosure, the load may not be a pre-determined level, but may be the maximum amount of force that can be generated by a piston 19. It is to be understood that a particular load may be more preferable depending on the architecture of the fluid injector used. For example, different types of syringes used in the same injector may result in different capacitance, and it may be preferable to set a different zero volume position based on different syringes.

Figure 7D:
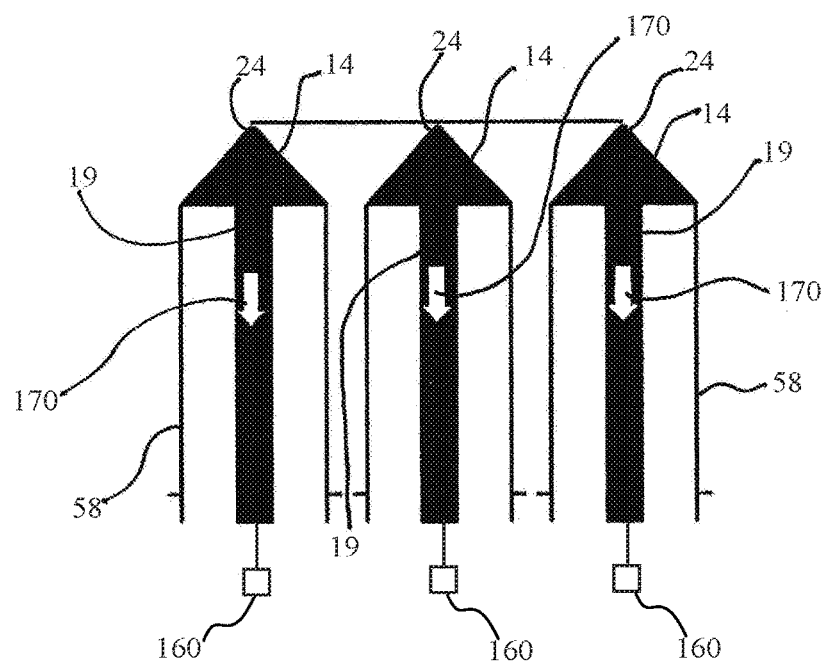
FIG. 7D is a schematic depiction according to FIG. 7A wherein the plungers are released.

With reference to FIG. 7D, when the load on each plunger 14 and/or plunger 19 is measured to be a predetermined level, the force exerted by the plunger 14 may be gradually lessened until the load force value measured by each of the sensors 160 is a second predetermined value, such as zero load force (i.e., when there is no reciprocal force or load, or some other predetermined value that is less than the predetermined level or range depicted by arrows 155 in FIG. 7C. In examples, the piston 19 may gradually be retracted in a proximal direction, or the force applied in the distal direction gradually may be released and the released load force may move the piston 19 in the proximal direction until a zero load force value is obtained. In examples consistent with the present disclosure, this may be a passive retraction which allows the potential energy created by the kinetic loading of the motor driving the pistons to unwind, or release, like a spring until it has reached a predetermined load less than that which was generated at maximum. The direction of the gradual proximal motion is depicted by arrows 170. The position or positions of the piston 19 in this state may be recorded or stored on a memory device, such as external or internal memory of a computing device or the fluid injector, not shown, and calibrated as the position of zero volume of fluid in the syringes, or the "zero volume" position. It is to be understood that the zero volume position may vary depending on the elasticity of the plunger 14, the piston 19, or other parameters of the fluid injector 10.

In examples consistent with the present disclosure, a mechanical stop can be utilized to identify the zero volume position. In a non-limiting example, this may comprise a trip switch set by the position reached by the plunger 14 and/or the piston 19 at maximum load.

The schematic depiction in FIGS. 7A-7D is not applicable only to a MUDS. It is to be understood that the schematic depiction therein also would apply to injectors 10 including syringes 12 according to FIG. 1 and/or FIG. 2, as well as rolling diaphragm syringes 34 according to FIG. 3 and FIG. 4. Embodiments may be applied to pre-filled syringes, as described herein.

It is to be understood that additional capacitance may exist in the syringes 12, 34, 58 at their respective distal ends 24, 40 even when the pistons 19, 52 are at the calibrated zero volume position. However, the zero volume position is to be understood to be the position when the piston 19, 52 is incapable of injecting any additional fluid during injection proceedings. In addition, the zero volume position may be utilized to accurately determine the volume of fluid held within the syringe at any time by comparison of the current piston position to the zero volume position.

Figure 8A:
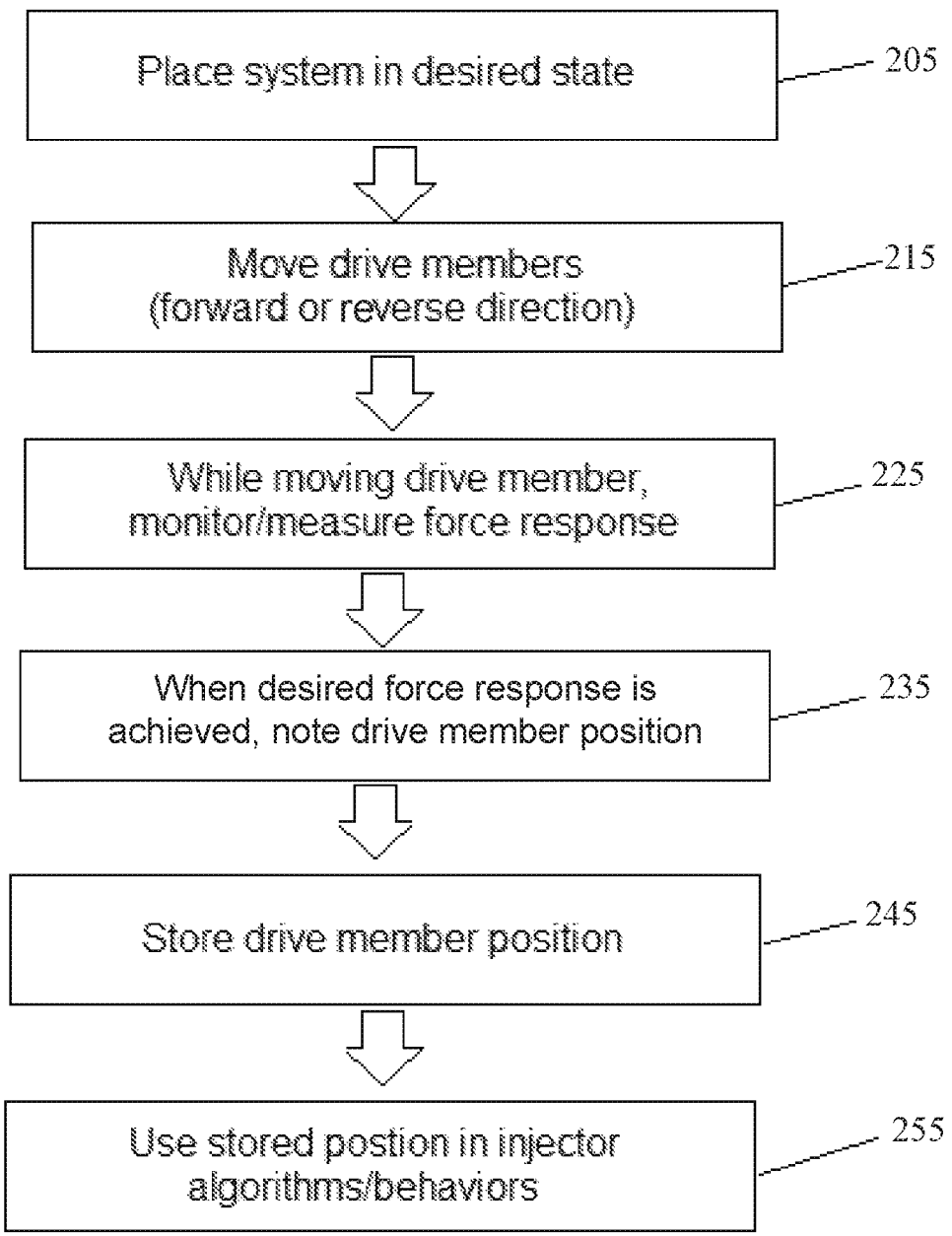
FIGS. 8A and 8B are flow charts depicting methods for calibrating the position of a drive mechanism of a fluid injector in accordance with examples according to the present disclosure.

FIG. 8A is flow chart illustrating an embodiment of a method of the present disclosure. According to these embodiments, the fluid injector system is placed into a state 205 in preparation for a calibration protocol, for example by installing the one or more fluid reservoirs, for example the at least one syringe 12, 58, 34, and engaging the respective drive members, such as a plunger, in operable communication with at least one piston 19. The drive members, such as the at least one piston 19, is driven 215 in a distal direction when pressurization of the fluid reservoir is desired or in the proximal direction when pulling a vacuum or relieving pressure is desired. While moving the drive member, the force response of the system may be monitored and/or measured 225 to determine a load force on the system. Once a desired fore response, as measured by load force, is achieved, the position of the drive member is determined and noted 235 by the injector processor 300 and stored 245 in the processor memory. The stored drive member position may then be used by the processor 300 of the injector 10 in stored algorithms and/or other programmed behaviors 255 as required by the stored injector protocols.

Figure 8B:
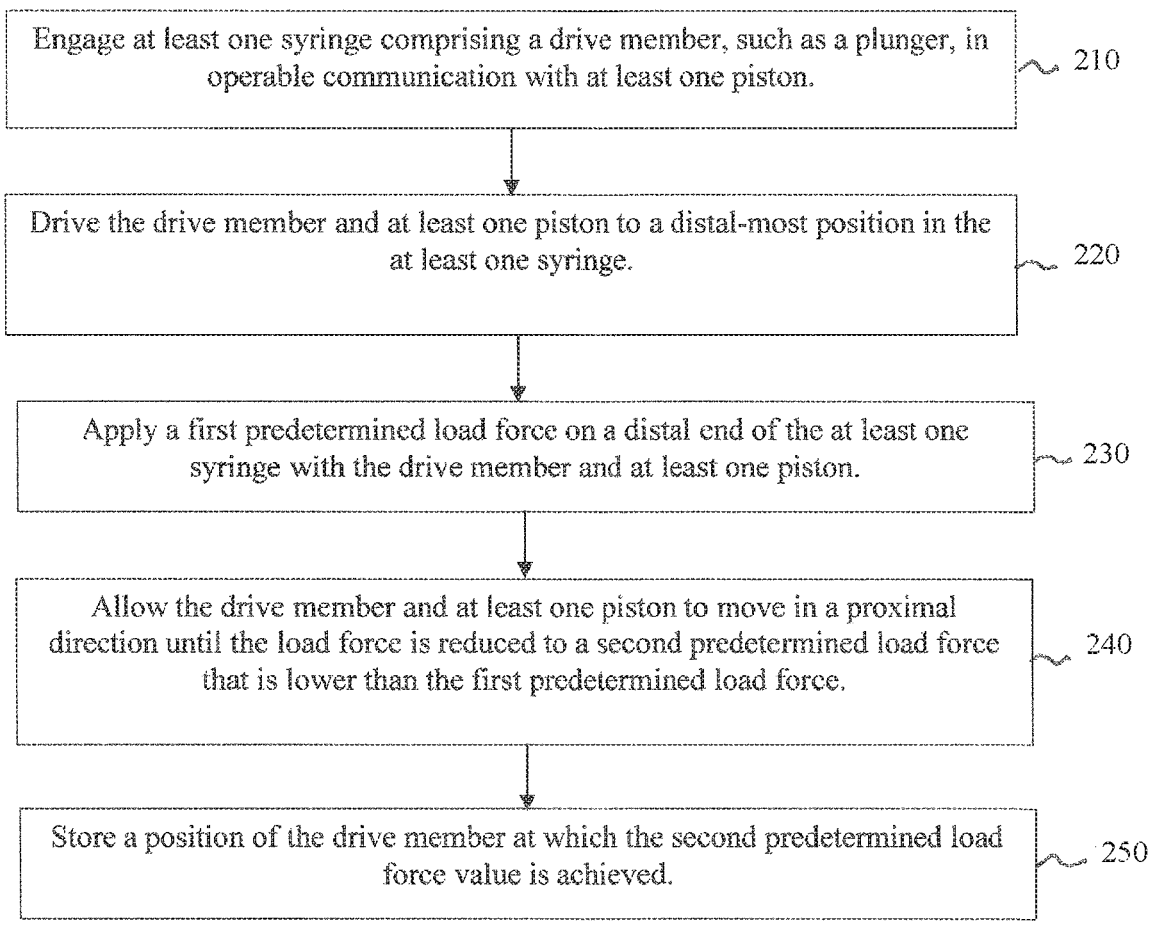

FIG. 8B is a flow chart depicting a method according to an embodiment of the present disclosure. Step 210 is to engage at least one syringe 12, 58, 34 comprising a drive member, such as a plunger, in operable communication with at least one piston 19. Step 220 is to drive the drive member and at least one piston 19 to a distal-most position in the at least one syringe 12, 58, 34. Step 230 is to apply a first predetermined load force on a distal end of the at least one syringe 12, 58, 34 with the drive member and at least one piston 19. The position of the drive member and at least one piston 19 in step 230 may be recorded in certain embodiments (not shown). Step 240 is to allow the drive member and at least one piston 19 to move in a proximal direction until the load force is reduced to a second predetermined load force that is lower than the first predetermined load force. In embodiments, the second predetermined load force may be zero. It is to be understood that the term "allow" according to step 240 is inclusive, in various examples, of driving the drive member and at least one piston 19 in a proximal direction, releasing or lessening force applied on the drive member in a distal direction. Step 250 is to store a position of the drive member at which the second predetermined load force value is achieved. It is to be understood that additional steps consistent with the present disclosure may be included in this method.

Figure 9:
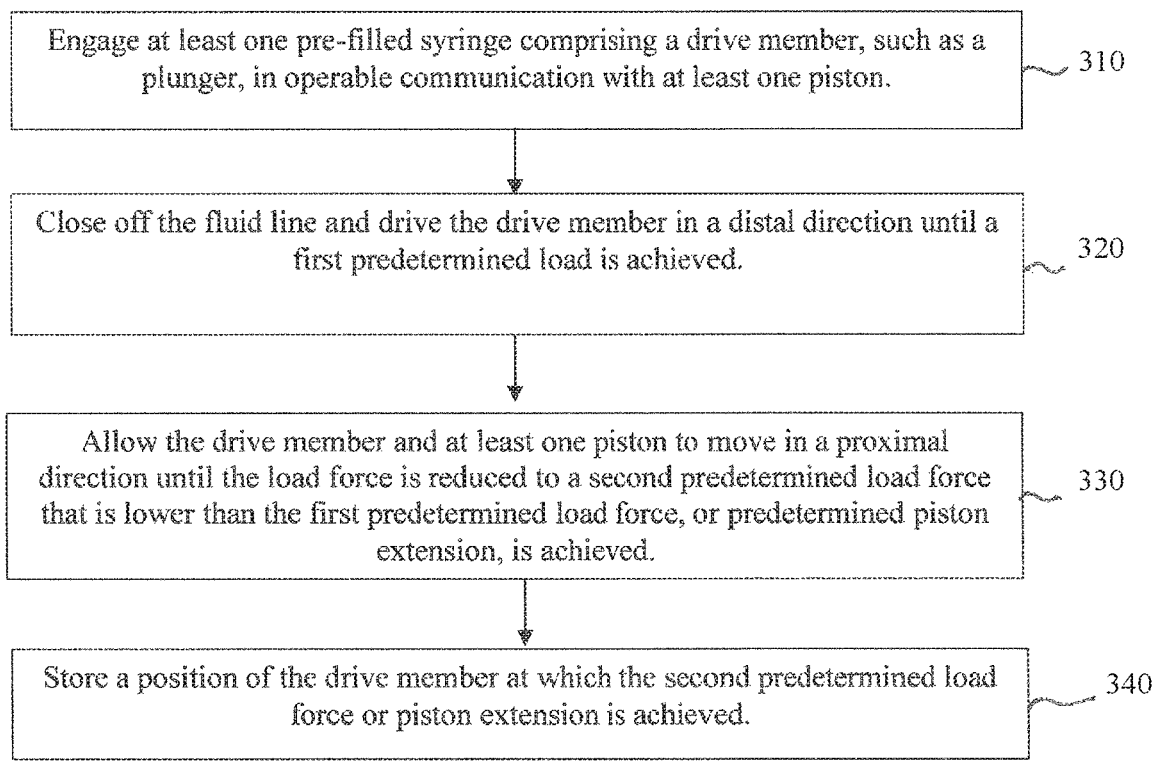
FIG. 9 is a flow chart depicting another method for calibrating the position of a drive mechanism of a fluid injector in accordance with an example according to the present disclosure.

FIG. 9 is a flow chart depicting another method according to an embodiment of the present disclosure. Step 310 is to engage at least one pre-filled syringe comprising a drive member, such as a plunger, in operable communication with at least one piston 19. Step 320 is to close off the fluid line and drive the drive member in a distal direction until a first predetermined load is achieved. Optionally, the piston extension in this state may be measured. Step 330 is to allow the drive member and at least one piston to move in a proximal direction until the load force is reduced to a second predetermined load force that is lower than the first predetermined load force, or a predetermined piston extension, is achieved. In embodiments, the second predetermined load force may be zero. It is to be understood that the term "allow" according to step 330 is inclusive, in various examples, of driving the drive member and at least one piston 19 in a proximal direction, releasing or lessening force applied on the drive member in a distal direction. Step 340 is to store a position of the drive member at which the second predetermined load force value or piston extension is achieved. It is to be understood that additional steps consistent with the present disclosure may be included in this method.

The system and method according to the present disclosure is beneficial because it allows calibration without the presence of medical fluid, thereby reducing waste and potential contamination.

Further, the various methods allow for monitoring of changes of zero volume position over time for a specific injector or syringe set up. Examples according to the present disclosure may be used to track wear on a syringe if the syringe is used multiple times by tracking changes in the zero volume position over multiple uses. In other examples, the method of the present disclosure may be used to track wear on a batch of syringes by tracking changes in the zero volume positions of the syringes in the batch. Further examples of the present disclosure may be used to track wear on the injector, such as by tracking changes in the zero volume position of the drive member of the injector. Over time, the anticipated position of the drive member may change due to wear on various components of the drive member. This may have applications in predictive maintenance of the injector, and the syringes.

Various embodiments according to the present disclosure may be used to determine whether a syringe is damaged (for example, whether the syringe is punctured or cracked) based on whether the determined zero volume position is at a more proximal or distal position than anticipated. The determined zero volume position may also be used to determine defects in a syringe or batch of syringes if the zero volume position is outside of expected parameters, such as factory settings.

According to examples consistent with the present disclosure, if the determined zero volume position is too proximal, a cocked or misaligned plunger may be indicated. If the determined zero volume position is too distal, another error or failure may be indicated, such as, for example a failure in the syringe or reservoir restraint where the restraint has failed or the tolerances have increased over the use life of the injector to a point where they fall outside the approved tolerances. Errors warning the user of these conditions may be returned by software in the memory of a computing device 300, and/or the injection procedure may be halted by the controller until the error has been rectified.

Examples according the present disclosure also may be used to determine the amount of recoil in a plunger, or recoil due to syringe capacitance. This may be used to determine whether the plunger and/or syringe is fit for use, or the amount of wear on the plunger and/or syringe.

Examples consistent with this disclosure may involve determining whether a syringe is new or used based on the zero volume position when compared to an expected zero volume position.

Examples consistent with this disclosure may be used to measure breakaway (i.e., static) and dynamic friction on the way up, at the start of the day or initial use of a multi-use syringe. The initially measured values for friction may be correlated with measured values over time. This may be used to assess silicone presence—or gross silicone absence—if the measured value falls outside the expected range or tolerance. This may be useful in order to assure the quality of the syringe production. This may be useful to measure the accuracy of the system's pressure prediction algorithm. For example, if silicone is not present, the running friction of the plunger will be high, and the system may mistake that frictional loss for pressure—disarming or limiting the injection.

Examples consistent with the present disclosure may be applied to pre-filled syringes. In a non-limiting example, an embodiment of the method and/or system herein may be applied to a pre-filled syringe with a closed stopcock prior to the start of an injection. The piston of a fluid injector may apply a load to a predetermined value, and the extension of the piston required to generate that load may be measured. Load applied to a piston or other drive member may be determined, for example, by a strain gauge, measured motor current or effort, or change in motor current/effort, a pressure sensor, force sensor, measured compression, and the like. This measurement, or a series of such measurements, may be utilized to calculate compliance values of the fluid injector, and those values can be used to over-drive the piston to provide a corrected volume of fluid during an injection procedure in a system using active fluid control. In embodiments, the calculated compliance values may be used to determine a zero volume position.

According to other embodiments, the present disclosure provides for a method for characterizing and correcting a fluid injector system for volume discrepancies associated with mechanical slack from injector components, component deflection under an applied force, and compliance due to volume expansion resulting from hydraulic pressurization of fluid delivery components.

According to various embodiments, the present disclosure provides methods and fluid injector systems configured for characterizing and correcting for fluid injection system slack. System slack, as defined herein, may lead to inaccuracies in fluid volume delivery and lowered image quality. System slack according to these methods may be determined on an open system or a closed system, depending on injector configuration. While various embodiments are described fully with a syringe-type fluid reservoir, similar methodologies may be applied to fluid injectors comprising peristaltic pump-based and compressible bag based fluid reservoirs and drive systems. According to certain embodiments including a closed (or selectively closable) system, the methods may include driving at least one drive member of a fluid injector, such as a piston engaged with a plunger or with the proximal end wall of a rolling diaphragm, to a distal end of at least one syringe connected to the fluid injector; retracting the at least one drive member toward a proximal end of the at least one syringe to draw in a volume of fluid, such as a liquid medical fluid, into the at least one syringe from at least one fluid container in fluid communication with the at least one syringe when the valve is in a first, fill position; switching at least one valve, which may be a stopcock, one-way valve, high pressure cracking valve, or pinch valve, from the first, fill position where the at least one syringe is in fluid communication with the at least one fluid container to a second, closed position where the at least one syringe is isolated from the at least one fluid container and the at least one syringe is isolated from the at least one part of the fluid injection system associated with delivering fluid to a patient, for example a fluid delivery path; measuring and storing a reference position of the at least one drive member within the at least one syringe filled with the volume of liquid fluid and in certain embodiments substantially no air; driving the at least one drive member toward the distal end of the at least one syringe until a desired load on the at least one drive member is reached as measured by a strain sensor, a force sensor, a pressure sensor, motor current or effort, or similar measurement; measuring and storing a contact position of the at least one drive member within the at least one syringe, wherein the contact position is a position where the desired load is reached; and deriving a slack correction volume based at least partially on the difference between the reference position and the contact position. The slack correction volume may then be stored within a memory of a processor associated with the fluid injector and used to determine more accurate fluid delivery volumes for the particular syringe, for example where the syringe is a multi-use syringe, multi-use syringe set, or multi-use injection reservoir. The slack correction value may also be used to provide more accurate fluid delivery volumes for subsequent similar syringes (e.g., syringes from same manufacturer and/or having the same fluid volume capacity) utilized by the injector system.

According to other embodiments, after filling the syringe with the medical fluid and moving the valve to the second, closed position, the method may involve pulling a vacuum on the fluid in the syringe by proximally retracting the drive member until a desired applied vacuum is achieved, as measured for example by strain sensor, a force sensor, a pressure sensor, motor current or effort, or similar measurement, and measuring the vacuum position of the drive member; releasing the applied retraction force on the drive member, either gradually, in a step-wise fashion, or at one time and allowing the drive member to return to a position where no vacuum force is applied to the drive member; measuring the neutral position of the drive member; and deriving a slack correction volume from the difference in volume of the fluid when the drive member is in the vacuum position and when the drive member is in the neutral position, where the slack correction volume includes a component associated with the mechanical slack of the drive member and motor associated with the at least one syringe.

As will be described for various embodiments, the processor may store and monitor a series of slack correction values over a time period and provide an alert when sudden deviations in the slack correction value are observed or the change in slack correction reaches a level indicating service of the injector is desired or required.

In various embodiments, the derived slack correction volume may be, at least in part, the difference of fluid volume ($\Delta V$) in the syringe under the desired load compared to the volume of the fluid in the syringe when the syringe is not under applied load, such as after drawing in fluid and closing of the valve. According to various embodiments, the desired applied load may be substantially similar to a load applied during a typical fluid injection, for example, from 1 psi to 300 psi for a CT injection or from 300 psi to 1,200 psi for an angiography injection. In other embodiments, the desired load may be equal to the amount of load necessary to take up all slack, with may be measured, for example by applying an increasing amount of load until no further movement of the drive member due to slack uptake is observed. The various components of the slack value include, but are not limited to, mechanical slack, deflection, compression of components under mechanical load or fluid pressure, such as compression of the plunger cover under fluid pressure, and volume expansion under fluid pressure of system components upstream of the valve, including the syringe sidewalls, valve components, and upstream fluid path surfaces.

In other examples of the present disclosure, after a slack correction volume has been determined, the method may further include evacuating the fluid from the at least one syringe, filling the at least one syringe with a desired volume of fluid plus an additional volume of fluid equal to the slack correction volume, and delivering the fluid from the at least one syringe to a patient. According to these embodiments, more accurate injection volumes and bolus sizes are produced, which may lead to increases in image quality.

In other embodiments of the present disclosure, the method steps may be performed at least partially by a processor configured to control a motor driving the at least one drive member of the fluid injector. The processor may include programming machine language to direct the processor to conduct the method at specified times.

In various embodiments, the method may include the system repeatedly determining and storing a slack correction volume over a specified time period, for example, at an initial use of the at least one syringe or at the beginning of the day, week, month, or other selected time period. Once repeated measurements have been taken and stored by the method for the slack correction volume over time, the method may further include the fluid injector, for example the processor, developing a slack curve for each drive member of the injector as a function of time. In certain embodiments, the method may then include providing an alert to a user if a measured slack correction volume for at least one drive member is significantly different from an expected slack correction volume based on the slack curve for the at least one drive member. According to other embodiments, the processor may monitor the slack correction volume, for example with a slack curve, and when a slack volume degrades to a certain value, the processor may alert the technician, hospital, or even notify the service personnel directly that service is desired or required.

In other examples of the present disclosure, a method for characterizing and correcting fluid injection system slack may include driving at least one drive member, for example a piston engaged with a syringe plunger or a proximal end wall of a rolling diaphragm syringe, of a fluid injector to a distal end of at least one syringe connected to the fluid injector; retracting the at least one drive member toward a proximal end of the at least one syringe to draw fluid, such as a liquid medical fluid, into the at least one syringe from at least one fluid container in fluid communication with the at least one syringe when the valve is in a first, fill position; switching at least one valve, which may be a stopcock, one-way valve, high pressure cracking valve, or pinch valve, from the first, fill position where the at least one syringe is in fluid communication with the at least one fluid container to a second, closed position where the at least one syringe is isolated from the at least one fluid container and the at least one syringe is isolated from the at least one part of the fluid injection system associated with delivering fluid to a patient, for example a fluid delivery path; driving the at least one drive member toward the distal end of the at least one syringe until a desired applied load on the at least one drive member is reached, as determined as described herein; measuring and storing a contact position of the at least one drive member within the at least one syringe where the at least one drive member is under the desired applied load; relieving the force associated with the desired applied load from the at least one syringe until a pressure within the at least one syringe is equal to where the at least one drive member has no applied load, where relieving the force may be affected by gradually releasing the applied load, releasing the applied load in a stepwise fashion, or by releasing all applied load at one time; measuring and, optionally, storing a reference position of the at least one drive member within the at least one syringe where the pressure within the at least one syringe is equal to where the at least one drive member has no applied load; and deriving a slack correction volume based at least partially on the difference between the reference position and the contact position. The derived slack correction volume from these embodiments may be utilized as described herein to provide improved fluid delivery accuracy and system performance monitoring.

In other examples of the present disclosure, the method may further include evacuating the fluid from the at least one syringe, filling the at least one syringe with a desired volume of fluid plus an additional volume of fluid equal to the slack correction volume, and delivering the fluid from the at least one syringe to a patient as part of a fluid injection protocol.

In other examples of the present disclosure, the method steps may be performed at least partially by a processor configured to control a motor driving the drive member of the injector.

In other embodiments as before, the method may include the system repeatedly determining and storing a slack correction volume over a specified time period, for example, at an initial use of the at least one syringe or at the beginning of the day, week, month, or other selected time period. Once repeated measurements have been taken and stored by the method for the slack correction volume over time, the method may further include the fluid injector, for example the processor, developing a slack curve for each drive member of the injector as a function of time. In certain embodiments, the method may then include providing an alert to a user if a measured slack correction volume for at least one drive member is significantly different from an expected slack correction volume based on the slack curve for the at least one drive member. According to other embodiments, the processor may monitor the slack correction volume, for example with a slack curve, and when a slack volume degrades to a certain value, the processer may alert the technician, hospital, or even notify the service personnel directly that service is desired or required.

Figure 10:
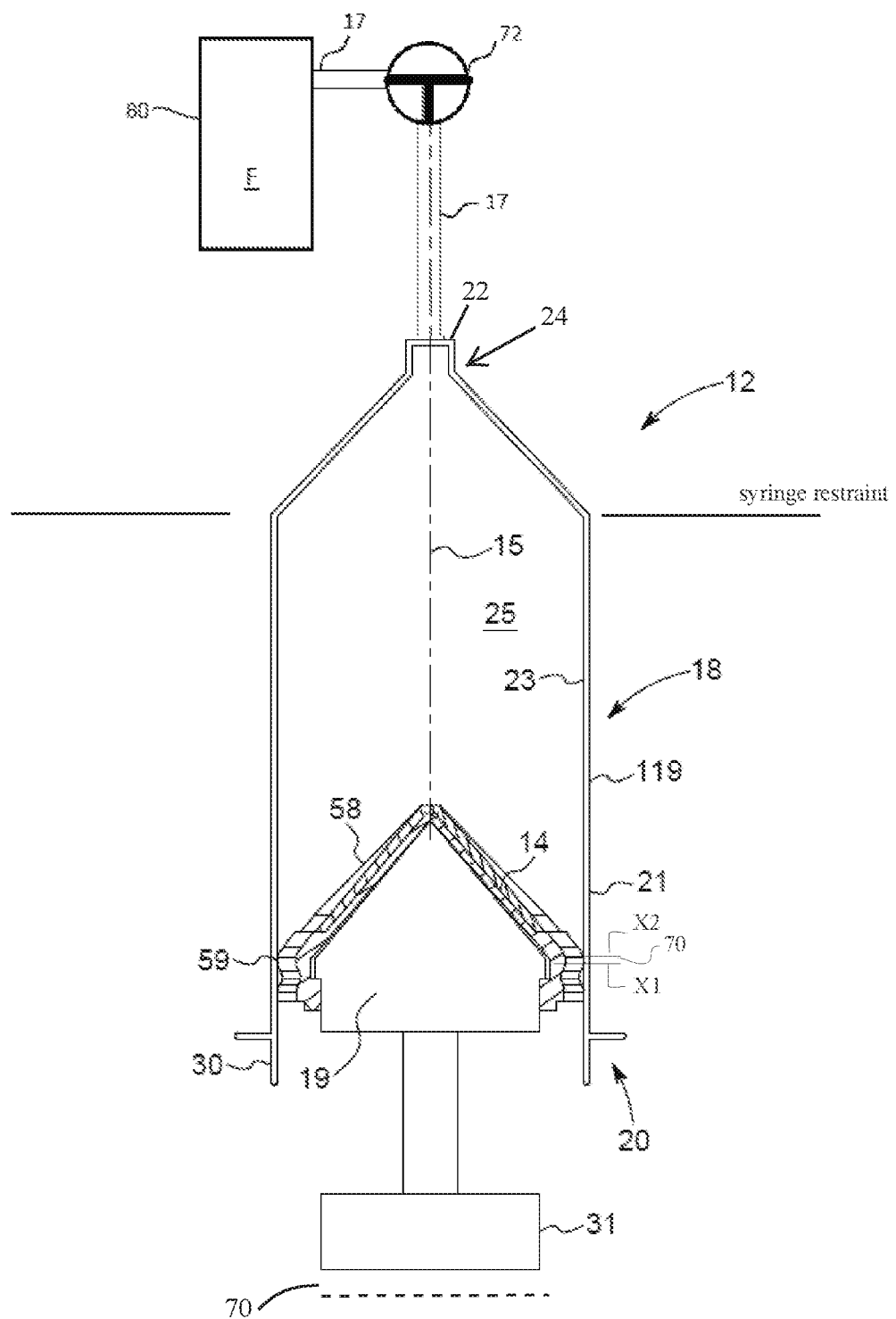
FIG. 10 is a cross-sectional view of the syringe of FIG. 6, illustrating slack between the piston and the plunger during a filling operation.

FIG. 10 shows the syringe 12 of FIG. 2 or 5, but illustrates an imperfect interface between a piston 19, and the plunger 14 of the syringe 12. The syringe 12 is shown in fluid communication with a valve 72 in a first position and a fluid container 80 storing a fluid F such as a contrast imaging agent, saline, or other medical fluid. The imperfect interface between the piston 19 and the plunger 14 permits slack 70 to propagate between the piston 19 and the plunger 14 when opposing loads are applied to the piston 19 and the plunger 14. Additional components of the slack may arise from tolerances, imperfect contact, and wear in injector components such as gears and mechanical connections associated with the piston 19 and motor 31 of the injector. For example, during a filling operation of the fluid injector 10, fluid F is drawn from the container 80 into the interior volume 25 of the syringe 12 by moving the plunger 14 from the distal end 24 to the proximal end 20 of the syringe 12. During the filling operation, the motor 31 draws the piston 19, which is connected to the plunger 14, towards the proximal end 20 of the syringe 12. Engagement between the plunger 14 and the piston 19 permit movement between the plunger 14 and the piston 19 allowing the slack 70 to propagate. Concurrently, friction between the periphery of the plunger 14 and the inner surface 23 of the sidewall 119 of the syringe 12 acts on the plunger 14 in the opposite direction of the piston 19, causing the plunger 14 to drag against the sidewall 119 as the piston 19 pulls the plunger 14 towards the proximal end 20 of the syringe 12. Also opposing proximal movement of the plunger 14 is a suction force created by pulling the fluid F from the container 80. These opposing forces on the plunger 14 cause the piston 19 and the plunger 14 to separate along the imperfect interface between them, producing at least a component of the slack 70 associated with the syringe and injector. These forces may also cause separation and slack between contacting components of the injector motor 31 and/or piston 19.

Figure 11:
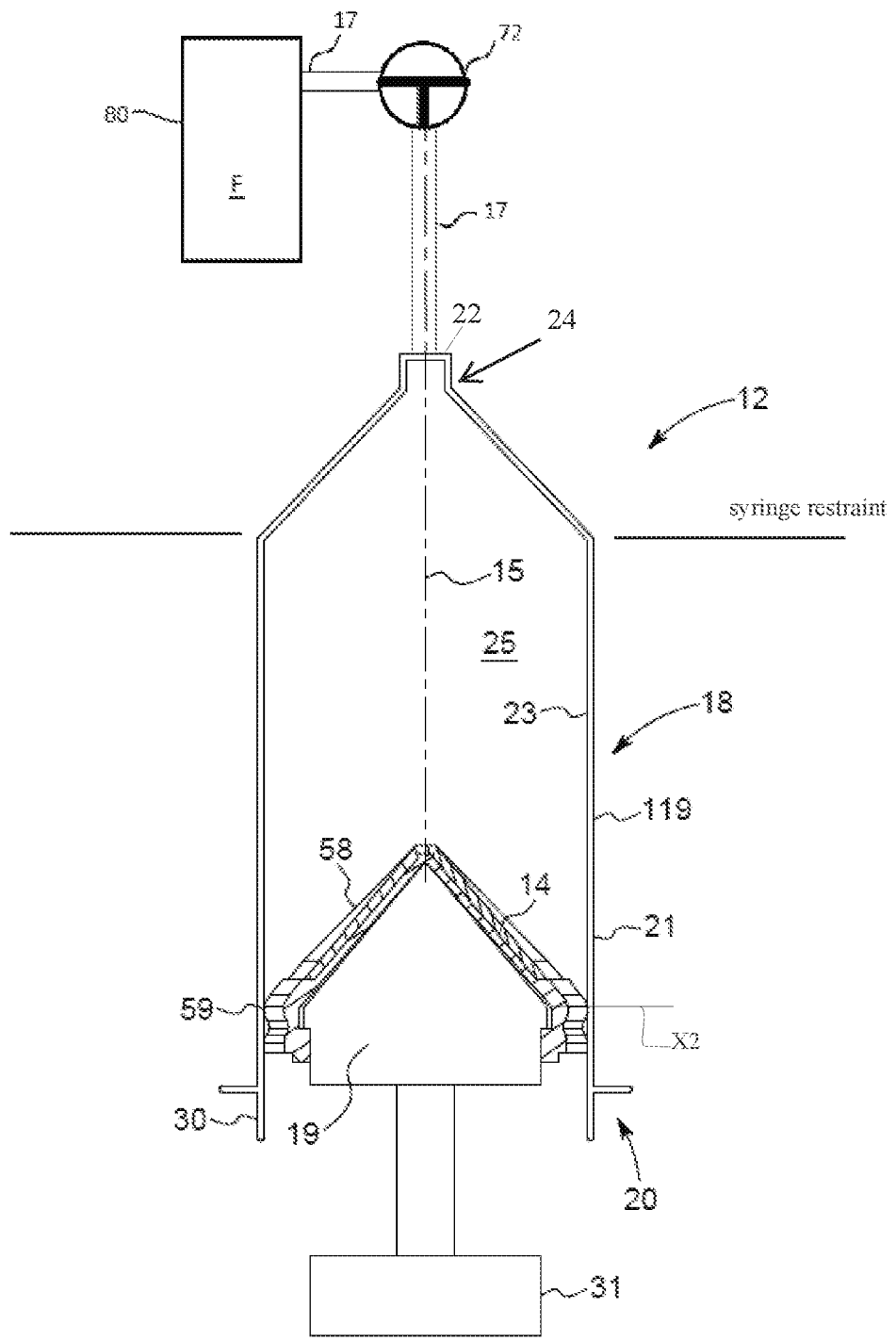
FIG. 11 is a cross-sectional view of the syringe of FIG. 6, illustrating the removal of slack during a delivery operation.

Referring now to FIG. 11, after switching of the valve from the first position with fluid communication between the syringe 12 and fluid container 80 to the second position where the syringe 12 is fluidly isolated from the fluid container 80 and patient fluid path (not shown) or to a third position with fluid communication between the syringe 12 and the patient fluid path, when the piston 19 transitions from the filling operation to a delivery operation, the slack 70 is removed as the motor 31 drives the piston 19 distally into the plunger 14 toward the distal end 22 of the syringe 12, for example, evacuating the fluid F from the barrel 18 and delivering it to the patient or if the system is a closed system and the fluid F in the syringe 12 is fluidly isolated from the other components, but compressing the fluid F. Fluid pressure within the barrel 18 and friction force between the plunger 14 and the sidewall 119 act to force the plunger 14 and piston 19 together to assist in the removal of the slack 70 due to the pinned connection between the plunger 14 and piston 19.

During the delivery operation, a portion of the total distal movement of the piston 19 is lost from removing the slack 70 due to the distance travelled pushing the piston 19 back into contact with the plunger 14 or the time required for the motion of the motor to move the piston 19 into full contact with the plunger 14. The plunger 14 does not move during this time and no fluid F is delivered to the patient during that time associated with motor movement and the distal movement of the piston 19. To account for this lost movement of the piston 19, the motor 31 of the injector 10 is programmed to overdrive the piston 19 farther in the distal direction than would be necessary to deliver the desired volume of fluid F if the slack 70 was absent. In other embodiments, the motor 31 may distally drive the piston 19 a distance corresponding to a calculated volume equal to the slack following any proximal movement of the piston 19 so that any subsequent distal movement of the piston 19 will have pre-compensated for the slack so that fluid delivery is accurate based on the pre-compensated piston position. In particular, processor 300 implementing software for controlling the motor 31 may be configured to characterize and correct for the slack 70 in the fluid delivery system. Further, slack values may be continually calculated and adjusted for to account for continuing wear to the injector over time.

The slack 70 between the piston 19 and plunger 14 as described herein is intended as an exemplary illustration of how one source of slack 70 propagates in the system. It is not to be construed as the principal or only source of slack 70 contemplated by the present disclosure. Other sources of slack 70 in the system are propagated and may be accounted for in a similar manner to provide improved accuracies for actual injection volumes. These sources of slack 70 may also include, but are not limited to, slack 70 from backlash on gears and/or ball screws in the motor 31, the interface between the syringe 12 and the injector 10, and any other surfaces which experience load during fluid injection. Other sources of slack in the system may be known to one of ordinary skill in the art and may be accounted for by the system and methods described herein, including the stacking of tolerances between the injector 10, syringe 12, and drive components.

The amount of slack 70 remains substantially the same for each cycle of filling and delivery operations of the injector 10 over a specific period of time, so long as the components of the injector 10 (e.g., disposable syringes, MUDS, etc.), particularly the piston 19 and plunger 14, are not changed, for example due to wear, during this period. As such, the slack calculation may not need to be constantly updated. Therefore, once the slack 70 is characterized for one cycle, the processor 300 may be programmed or configured to account for the slack 70 for any subsequent cycles by converting the slack 70 into an overdrive distance or volume necessary to deliver the desired amount of the fluid F. The slack 70 may also be continually monitored, for example if there is particular concern with component wear in a particular configuration. The process of deriving a slack correction volume is set forth with reference to FIGS. 12 and 10. Hereinafter, any sequence or method steps are understood to be implemented by the processor 300, but, where context allows, may also be implemented by a technician, physician, nurse, or the like.

Figure 12:
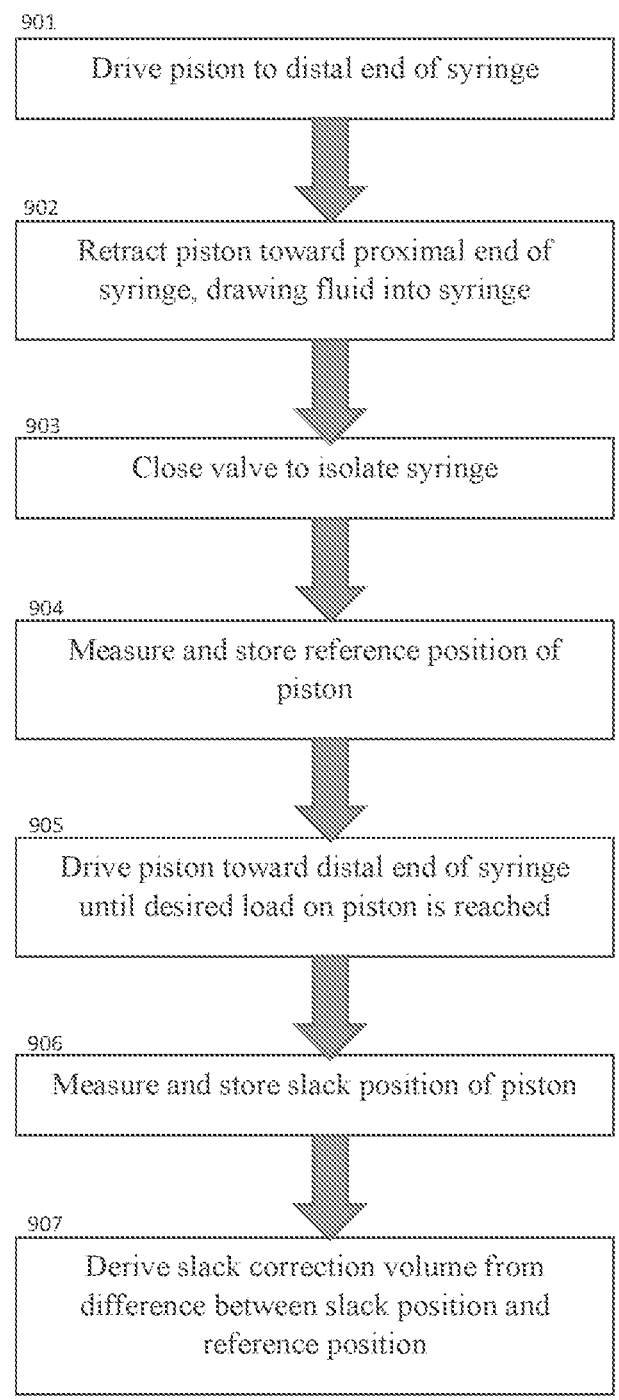
FIG. 12 is a step diagram of a method according to an example of the present disclosure.

A step diagram for characterizing the slack 70 according to one example of the present disclosure is illustrated in FIG. 12. First, at step 901, the injector 10 and syringe 12 are setup with the piston 19 extended distally such that the plunger 14 is located at an end-of-travel position towards the distal end 24 of the barrel 18. Next, at step 902, the plunger 14 is retracted by the piston 19 via operation of the motor 31 toward the proximal end 20 of the syringe 12, drawing a predetermined volume of the fluid F from the container 80 into the interior volume 25 of the syringe 12. As an initial part of step 902, the fluid path set 17 may be purged of air by first drawing a partial volume of fluid F into the syringe 12 and then driving the piston 19 distally to force the fluid F through the fluid path set 17 to displace the air. Purging the air may be necessary to accurately measure the slack 70 in the system. After purging the fluid path set 17 of air, the remaining fluid necessary to achieve the predetermined volume of the fluid F may be drawn into the syringe 12. The predetermined volume of the fluid F may be equal to the volume intended for delivery to the patient, plus an additional slack volume to account for the slack 70 between the piston 19 and the plunger 14 and any necessary excess volume necessary to correct for system capacitance and impedance. For example, if the intended fluid volume for delivery to the patient is 200 milliliters and the system slack is determined to be 10 milliliters, the plunger 14 may be drawn back to the 210 milliliter position and then driven forward to the 200 milliliter position to account for the 10 milliliters of slack 70. In other examples, the predetermined volume of the fluid F may not be the intended fluid volume for delivery to the patient, but rather some intermediate volume to determine the slack 70 at some intermediate time of the delivery operation. Regardless of the predetermined volume, the additional slack volume at this stage may be derived from methods for characterizing slack as described herein.

The valve 72, which may be, for example, a stopcock valve, is then switched at step 903 to a position isolating the syringe 12 from the container 80. The position of the piston 19 is measured and stored as reference position X1 at step 904 (see FIG. 10). The motor 31 is then driven to move the piston 19 toward the distal end 24 of the syringe 12 step 905.

Because the valve 72 is in the second, closed position, none of the fluid F is actually delivered to the patient, causing pressure to build in the fluid F between the plunger 14 and the valve 72. This rising pressure results from the piston 19 moving in a distal direction, pressing the piston 19 and plunger 14 together and compressing the fluid F and the plunger surface. Compression between the piston 19 and the plunger 14 to remove the slack 70. The piston 19 is driven in the distal direction until a desired load on the piston 19 is reached. In some examples, the desired load may be the load at which fluid is to be delivered to the patient under a normal delivery operation, such as in the range of 0 psi to 300 psi, for example 50 psi. More generally, the desired load is determined based on contact between the plunger 14 and the piston 19.

Figure 14:
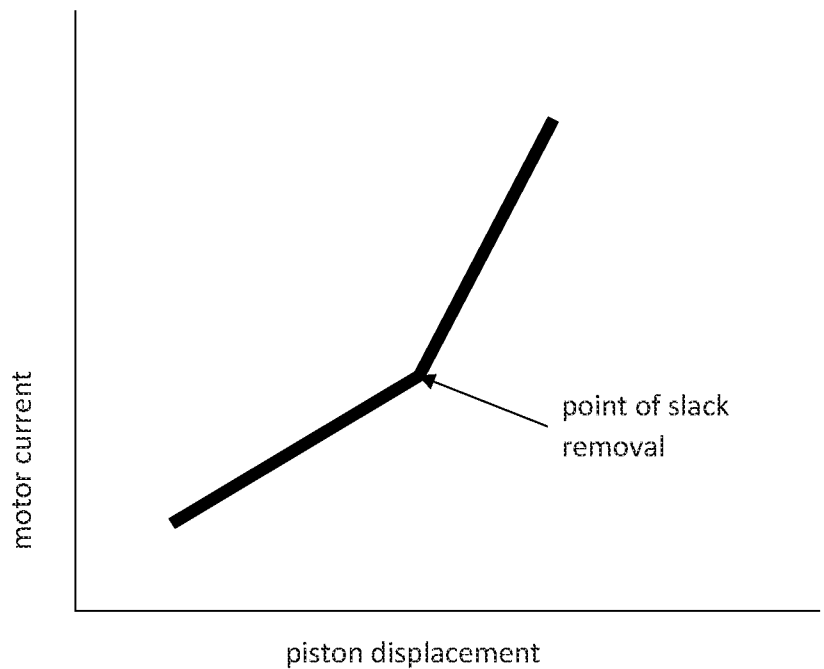
FIG. 14 is a graph of motor current versus piston displacement used to determine a point of slack removal from the fluid delivery system.
Figure 15:
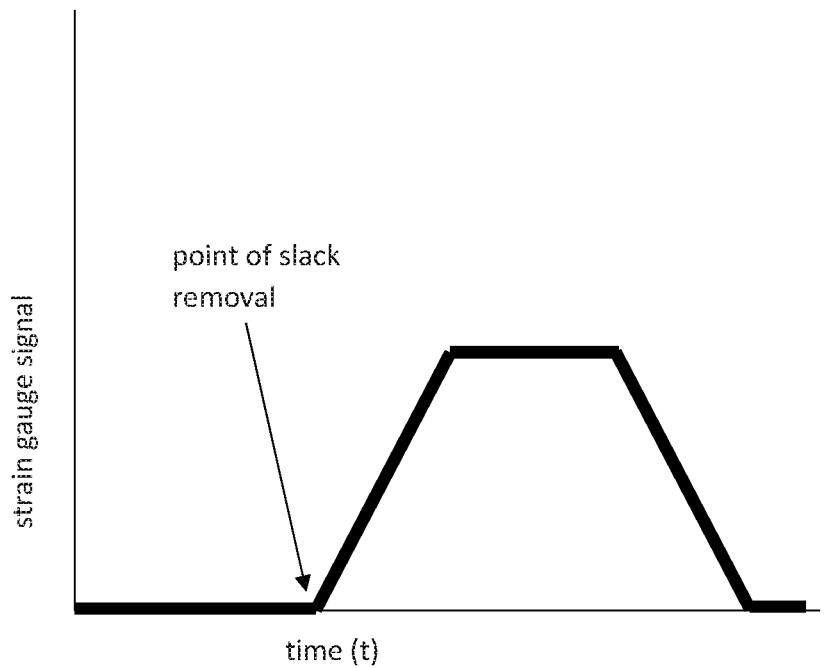
FIG. 15 is a graph of strain gauge signal versus time used to determine a point of slack removal from the fluid delivery system.

Several methods may be utilized for determining when the piston 19 has attained the desired load. For example, pressure may be directly measured by a transducer at any location between the syringe 12 and the valve 72. In other examples, the load may be derived from the current of the motor 31 or from deformation of any component between the syringe 12 and the valve 72. In other examples, the load may be determined from a strain gauge located on some component of the injection 10 or syringe 12, particularly the piston 19. In other examples, the load may be determined by deformation of the restraint holding the syringe 12 to the injector 10. FIGS. 14-15 show graphical representations of slack removal using current of the motor 31 and the signal from the strain gauge, respectively.

Once the desired load has been reached, the position of the piston 19 is again measured and stored as contact position X2 at step 906 (see FIG. 10). The difference between contact position X2 and the reference position X1 indicates the amount of slack 70 in the system that will be removed during each delivery operation of the injector 10. At step 907, a slack correction volume may be derived by subtracting the volume between the conical engagement surfaces of the piston 19 and the plunger 14 at the reference position X1 from the volume between the conical engagement surfaces of the piston 19 and the plunger 14 at the contact position X2. The slack correction volume is then stored for use as the additional volume of fluid F to draw from the container 80 in subsequent filling operations. Alternatively, the slack correction may be determined as the time at a specific piston movement rate to move the piston from the reference position X1 to the contact position X2. In this manner, the exact amount of additional movement of the piston 19 may be executed during each transition from a filling operation to a delivery operation, and vice versa. In other embodiments, the distal movement of the piston 19 to account for the volume due to the slack correction may be done after any proximal movement of the piston 19, even if not immediately transitioning to fluid delivery by further distal movement of the piston, so that the slack volume has been accounted for the next distal movement of the syringe. Thus, the fluid reservoir is pre-corrected and any distal movement has accounted for the slack, thereby accurately beginning fluid delivering and minimizing any time to actual fluid delivery due to slack. The determined value of the slack 70 may be used during each subsequent delivery operation, preventing under delivery, over delivery, waste and spillage of fluid, and pressure damage to system components. Following the attainment of the slack correction volume at step 907, pressure may be relieved from the syringe 12.

Figure 13:
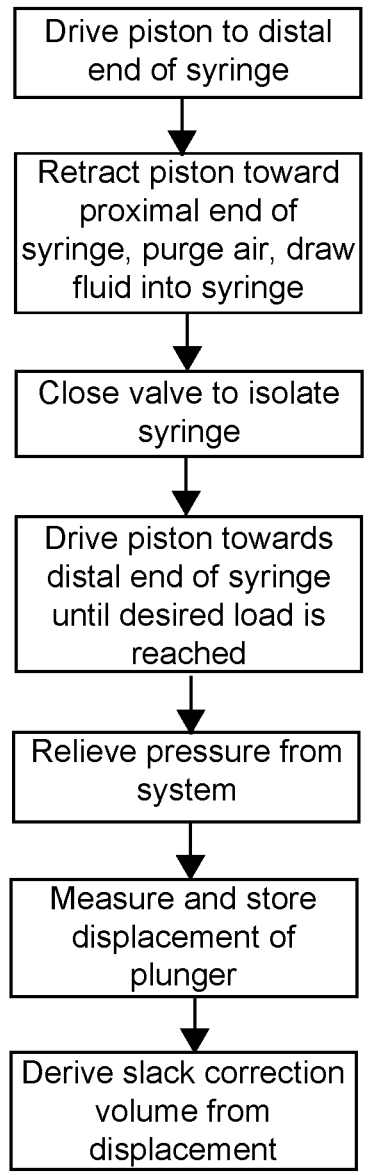
FIG. 13 is a step diagram of a method according to another example of the present disclosure.

In other examples of the present disclosure, the reference position X1 is measured after the syringe 12 is pressurized, as illustrated in the step diagram of FIG. 13. In such examples, the injector 10 and syringe 21 are setup with the piston 19 extended distally at step 1001, the piston 19 is retracted to draw a predetermined volume of the fluid F from the container 80 into the interior volume 25 at step 1002, and the valve 72 is switched to a second, closed position at step 1003. Steps 1001-1003 are performed substantially as described above in reference to steps 901-903 of FIG. 12, including the purging of air from the fluid path set 17. The piston 19 is then driven in the distal direction until a desired load on the piston 19 is reached at step 1004, substantially as described above in reference to step 905 of FIG. 12. The drive current is then removed from the motor 31 to relieve the applied pressure in the system at step 1005, allowing unwanted pressure to be removed from the fluid path set 17. The displacement of the position of the plunger 14 is then measured and stored while the slack 70 is removed from the system at step 1006. Accuracy may be enhanced by measuring the displacement of the plunger 14 rapidly upon relieving pressure in the system. At step 1007, the slack correction volume is calculated and stored substantially based on the displacement measured at step 906. In particular, the slack correction volume may be derived by converting the displacement measured at step 906 to a volume between the conical engagement surfaces of the piston 19 and the plunger 14 at the reference position X1 from the volume between the conical engagement surfaces of the piston 19 and the plunger 14 at the contact position X2. The slack correction volume is then stored for use as the additional volume of fluid F to draw from the container 80 in subsequent filling operations.

In other examples, the step of relieving pressure from the syringe 12 in the method of either of FIG. 12 or 13 may occur at alternative times during the execution of the methods to remove unwanted and/or undesirable pressure. For example, in the method described with reference to FIG. 12, pressure relief may be performed prior to measuring and storing the contact position X2 at step 906.

Characterizing and storing the slack 70 according to the systems and methods described herein is particularly suited for use during the initial filling of each disposable component, such as the syringe 12, when the disposable component is placed into service. However, the present disclosure is not limited in the time and manner of implementation. In other examples of the present disclosure, characterizing and storing the slack 70 may be performed at periodic intervals, such as each injection, each day, each week, or each month throughout the life of the injector 10 to recalibrate for component wear.

In other examples of the present disclosure, the measured slack 70 may be used in a statistical analysis or as part of a predictive maintenance protocol to intelligently alert users and/or service technicians that an injector 10, syringe 12, diaphragm syringe 34, and/or MUDS 56 is operating abnormally or otherwise requires service. According to this embodiment, a slack curve based on repeated slack volume measurements as a function of time may be prepared. At a selected time, a new slack measurement may be taken and compared to the slack curve. Any significant or unexpected deviation of the measured slack from that expected from the slack curve may be indicative of unexpected wear or potential failure of the mechanical components of the injector 10 or potential issues with a particular syringe set. The system may then alert the user of the abnormal reading so that a new syringe set may be installed and/or a service call may be scheduled.

While the systems and method for characterizing and correcting for slack 70 have been described herein with particular reference to the injectors 10 and syringes 12 substantially as shown in FIGS. 1-3, it is to be understood that these systems and methods could equally be applied to alternative syringe and/or injector configurations, such as the syringe, fluid delivery system, and multi-patient disposable system of FIGS. 4, 5, and 6, respectively, and with prefilled syringes which may be used in the present fluid injector systems.

Although the disclosure has been described in detail for the purpose of illustration based on what is currently considered to be the most practical and preferred examples, it is to be understood that such detail is solely for that purpose and that the disclosure is not limited to the disclosed examples, but, on the contrary, is intended to cover modifications and equivalent arrangements. For example, it is to be understood that the present disclosure contemplates that, to the extent possible, one or more features of any example can be combined with one or more features of any other example.

The invention claimed is:

1. A method for characterizing and correcting fluid injection system slack, the method comprising:
   driving at least one drive member of a fluid injector to a distal end of at least one syringe connected to the fluid injector;
   retracting the at least one drive member toward a proximal end of the at least one syringe to draw fluid into the at least one syringe from at least one fluid container in fluid communication with the at least one syringe;
   switching at least one valve from a first position where the at least one syringe is in fluid communication with the at least one fluid container to a second position where the at least one syringe is isolated from the at least one fluid container to isolate the at least one syringe from at least one part of the fluid injection system;
   measuring and storing a reference position of the at least one drive member within the at least one syringe;
   driving the at least one drive member toward the distal end of the at least one syringe until a desired load on the at least one drive member is reached;
   measuring and storing a contact position of the at least one drive member within the at least one syringe, wherein the contact position is a position where the desired load is reached; and
   deriving a slack correction volume based at least partially on a difference between the reference position and the contact position.

2. The method of claim 1, further comprising:
   evacuating the fluid from the at least one syringe;
   filling the at least one syringe with a desired volume of fluid plus an additional volume of fluid equal to the slack correction volume; and
   delivering the fluid from the at least one syringe to a patient.

3. The method of claim 1, further comprising repeatedly measuring and storing the slack correction volume over time to develop a slack curve of the at least one drive member of the at least one injector as a function of time.

4. The method of claim 3, further comprising alerting a user if a measured slack correction volume for the at least one drive member is substantially different from an expected slack correction volume based on the slack curve for the at least one drive member.

5. A method for characterizing and correcting fluid injection system slack, the method comprising:
   driving at least one drive member of a fluid injector to a distal end of at least one syringe connected to the fluid injector;
   retracting the at least one drive member toward a proximal end of the at least one syringe to draw fluid into the at least one syringe from at least one fluid container in fluid communication with the at least one syringe;
   switching at least one valve from a first position where the at least one syringe is in fluid communication with the at least one fluid container to a second position where the at least one syringe is isolated from the at least one fluid container to isolate the at least one syringe from at least one part of the fluid injection system;
   driving the at least one drive member toward the distal end of the at least one syringe until a desired load on the at least one drive member is reached;
   measuring and storing a contact position of the at least one drive member within the at least one syringe;
   relieving pressure from the at least one syringe until a pressure within the at least one syringe is equal to where the at least one drive member has no applied load;
   measuring and storing a reference position of the at least one drive member within the at least one syringe where the pressure within the at least one syringe is equal to the pressure applied by the at least one drive member; and
   deriving a slack correction volume based at least partially on a difference between the reference position and the contact position.

6. The method of claim 5, further comprising:
   evacuating the fluid from the at least one syringe;
   filling the at least one syringe with a desired volume of fluid plus an additional volume of fluid equal to the slack correction volume; and
   delivering the fluid from the at least one syringe to a patient.

7. The method of claim 5, further comprising repeatedly measuring and storing the slack correction volume over time to develop a slack curve of the at least one drive member of the at least one injector as a function of time.

8. The method of claim 7, further comprising alerting a user if a measured slack correction volume for the at least one drive member is substantially different from an expected slack correction volume based on the slack curve for the at least one drive member.

* * * * *

UNITED STATES PATENT AND TRADEMARK OFFICE
CERTIFICATE OF CORRECTION

PATENT NO.       : 11,786,652 B2
APPLICATION NO.  : 16/623828
DATED            : October 17, 2023
INVENTOR(S)      : McDermott et al.

It is certified that error appears in the above-identified patent and that said Letters Patent is hereby corrected as shown below:

On the Title Page

On Page 7, item (56), under "OTHER PUBLICATIONS", in Column 2, Line 24, delete "Magentic" and insert -- Magnetic --, therefor.

In the Specification

In Column 11, Line 40, delete "and or" and insert -- and/or --, therefor.
In Column 13, Line 45, delete "other" and insert -- in other --, therefor.
In Column 13, Line 50, delete "clam shell-type" and insert -- clamshell-type --, therefor.
In Column 15, Line 47, delete "and or" and insert -- and/or --, therefor.
In Column 18, Lines 64-65, delete "(wifi, Bluetooth etc.)" and insert -- (Wi-Fi, Bluetooth, etc.) --, therefor.
In Column 19, Line 62, delete "the a" and insert -- the --, therefor.
In Column 22, Line 37, delete "(i.e.," and insert -- i.e., --, therefor.
In Column 23, Line 14, delete "is flow" and insert -- is a flow --, therefor.
In Column 24, Line 55, delete "according" and insert -- according to --, therefor.
In Column 26, Line 60, delete "with" and insert -- which --, therefor.
In Column 29, Line 54, delete "for to" and insert -- to --, therefor.

Signed and Sealed this
Second Day of January, 2024

Katherine Kelly Vidal
*Director of the United States Patent and Trademark Office*